United States Patent
Alexander-Bridges et al.

(10) Patent No.: US 9,272,049 B2
(45) Date of Patent: *Mar. 1, 2016

(54) METHODS OF STIMULATING FAT MOBILIZATION USING A POLYMER CONJUGATED POLYPHENOL

(75) Inventors: Maria Alexander-Bridges, Thousand Oaks, CA (US); Shaker A. Mousa, Wynantskill, NY (US); Paul J. Davis, West Sand Lake, NY (US)

(73) Assignee: NANOPHARMACEUTICALS LLC, Rensselaer, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/156,047

(22) Filed: Jun. 8, 2011

(65) Prior Publication Data

US 2012/0258069 A1    Oct. 11, 2012

Related U.S. Application Data

(63) Continuation of application No. 11/992,152, filed as application No. PCT/US2006/036243 on Sep. 18, 2006, now abandoned.

(60) Provisional application No. 60/718,105, filed on Sep. 16, 2005.

(51) Int. Cl.
*A61K 31/22* (2006.01)
*A61K 47/48* (2006.01)

(52) U.S. Cl.
CPC ......... *A61K 47/48215* (2013.01); *A61K 47/482* (2013.01); *A61K 47/4823* (2013.01); *A61K 47/48176* (2013.01)

(58) Field of Classification Search
CPC .................. A61K 36/00; A61K 47/48215
USPC ..................... 514/546, 909; 424/725, 776
See application file for complete search history.

(56) References Cited

U.S. PATENT DOCUMENTS

| | | |
|---|---|---|
| 3,625,214 A | 12/1971 | Higuchi |
| 4,205,058 A | 5/1980 | Wagner et al. |
| 4,650,751 A | 3/1987 | Siegel et al. |
| 4,789,734 A | 12/1988 | Pierschbacher |
| 4,801,504 A | 1/1989 | Burdick et al. |
| 4,801,575 A | 1/1989 | Pardridge |
| 4,906,474 A | 3/1990 | Langer et al. |
| 4,925,673 A | 5/1990 | Steiner et al. |
| 4,968,590 A | 11/1990 | Kuberasampath et al. |
| 5,011,486 A | 4/1991 | Aebischer et al. |
| 5,091,513 A | 2/1992 | Huston et al. |
| 5,104,895 A | 4/1992 | Spinelli et al. |
| 5,158,978 A | 10/1992 | Rubin |
| 5,225,204 A | 7/1993 | Chen et al. |
| 5,231,000 A | 7/1993 | Majocha et al. |
| 5,304,121 A | 4/1994 | Sahatjian |
| 5,410,016 A | 4/1995 | Hubbell et al. |
| 5,438,126 A | 8/1995 | DeGroot et al. |
| 5,482,719 A | 1/1996 | Guillet et al. |
| 5,571,840 A | 11/1996 | Mayor et al. |
| 5,591,709 A | 1/1997 | Lindenbaum |
| 5,593,688 A | 1/1997 | Baldeschwieler |
| 5,648,506 A | 7/1997 | Desai et al. |
| 5,766,635 A | 6/1998 | Spenleuhauer et al. |
| 6,139,870 A | 10/2000 | Verrecchia |
| 6,316,412 B1 | 11/2001 | Ginsberg et al. |
| 6,414,037 B1 | 7/2002 | Pezzuto et al. |
| 6,482,406 B1 | 11/2002 | Stewart |
| 6,677,473 B1 | 1/2004 | Madison et al. |
| 6,740,680 B1 | 5/2004 | Danforth, Jr. et al. |
| 6,818,620 B2 | 11/2004 | Bhatnagar |
| 6,821,947 B2 | 11/2004 | Iozzo |
| 7,166,155 B2 | 1/2007 | Ishikawa |
| 7,638,558 B2 | 12/2009 | Breitenkamp et al. |
| 7,785,632 B2 | 8/2010 | Mousa et al. |
| 7,807,621 B2 | 10/2010 | Mazar et al. |
| 8,026,209 B2 | 9/2011 | Gaillard et al. |
| 8,071,134 B2 | 12/2011 | Mousa et al. |
| 8,242,171 B2 * | 8/2012 | Sinclair et al. ................ 514/546 |
| 8,518,451 B2 | 8/2013 | Mousa et al. |
| 8,668,926 B1 | 3/2014 | Davis et al. |
| 8,802,240 B2 | 8/2014 | Davis et al. |
| 2001/0021763 A1 * | 9/2001 | Harris .............................. 528/75 |
| 2001/0046521 A1 | 11/2001 | Zasloff et al. |

(Continued)

FOREIGN PATENT DOCUMENTS

| | | |
|---|---|---|
| CA | 2673133 A1 | 11/2008 |
| CN | 1126589 | 7/1996 |

(Continued)

OTHER PUBLICATIONS

Office Action (Mail Date Mar. 12, 2014) for U.S. Appl. No. 12/947,389, filed Jun. 16, 2010.

(Continued)

*Primary Examiner* — Prema Mertz
(74) *Attorney, Agent, or Firm* — Schmeiser, Olsen & Watts, LLP

(57) ABSTRACT

Provided herein are compositions and methods for preventing and treating diseases and risk factors associated with metabolic syndrome by targeting the RGD-binding site of selected intra- and extracellular proteins. Exemplary compositions include RGD-polyphenol conjugates via an ester linkage; polyphenol polymer conjugated to RGD analogs or mimetics; and RGD polymer conjugates linked to polyphenol.

5 Claims, 7 Drawing Sheets

(56) References Cited

U.S. PATENT DOCUMENTS

| | | |
|---|---|---|
| 2002/0049247 A1 | 4/2002 | Chen |
| 2002/0137676 A1 | 9/2002 | Hsiang et al. |
| 2002/0151594 A1 | 10/2002 | Morkin et al. |
| 2003/0027940 A1 | 2/2003 | Lang et al. |
| 2003/0138557 A1 | 7/2003 | Allison |
| 2003/0157098 A1 | 8/2003 | Laug |
| 2003/0162758 A1 | 8/2003 | Schwartz et al. |
| 2003/0165576 A1 | 9/2003 | Fujii et al. |
| 2004/0013728 A1* | 1/2004 | Oh et al. .................. 424/468 |
| 2004/0033259 A1 | 2/2004 | Hanshew, Jr. et al. |
| 2005/0124862 A1* | 6/2005 | Mousa et al. ............. 600/300 |
| 2005/0158376 A1* | 7/2005 | Sardi et al. .............. 424/451 |
| 2005/0171027 A1* | 8/2005 | Sinclair et al. ............ 514/25 |
| 2005/0222387 A1 | 10/2005 | Debatin et al. |
| 2005/0249721 A1 | 11/2005 | Houston et al. |
| 2005/0272817 A1 | 12/2005 | Heino |
| 2006/0166303 A1 | 7/2006 | Spanuth |
| 2006/0210539 A1 | 9/2006 | Zhang |
| 2007/0117841 A1 | 5/2007 | Ozes et al. |
| 2007/0190160 A1 | 8/2007 | Turos et al. |
| 2008/0124280 A1 | 5/2008 | Mousa et al. |
| 2008/0193377 A1 | 8/2008 | Line et al. |
| 2009/0022806 A1 | 1/2009 | Mousa et al. |
| 2009/0175862 A1 | 7/2009 | Silverio et al. |
| 2010/0112079 A1 | 5/2010 | Mousa et al. |
| 2010/0159021 A1 | 6/2010 | Davis et al. |
| 2010/0209382 A1 | 8/2010 | Alexander-Bridges et al. |
| 2010/0255108 A1 | 10/2010 | Lin et al. |
| 2011/0052715 A1 | 3/2011 | Davis et al. |
| 2011/0142941 A1 | 6/2011 | Davis et al. |
| 2012/0315320 A1 | 12/2012 | Davis et al. |
| 2014/0072635 A1 | 3/2014 | Mousa et al. |
| 2014/0072646 A1 | 3/2014 | Mousa et al. |
| 2014/0199375 A1 | 7/2014 | Mousa et al. |

FOREIGN PATENT DOCUMENTS

| | | |
|---|---|---|
| WO | 9500135 | 1/1995 |
| WO | 9640048 | 12/1996 |
| WO | 9833942 | 8/1998 |
| WO | 9856771 | 12/1998 |
| WO | 9958119 A1 | 11/1999 |
| WO | 9962549 | 12/1999 |
| WO | 0064431 A1 | 11/2000 |
| WO | 0078815 A1 | 12/2000 |
| WO | 0113031 A2 | 2/2001 |
| WO | 0113936 A1 | 3/2001 |
| WO | 0176589 A1 | 10/2001 |
| WO | 0203914 A2 | 1/2002 |
| WO | 0249501 A2 | 6/2002 |
| WO | 02060389 A2 | 8/2002 |
| WO | 03075741 A2 | 9/2003 |
| WO | 2004013728 A2 | 2/2004 |
| WO | 2004069201 A2 | 8/2004 |
| WO | 2005027895 A2 | 3/2005 |
| WO | 2006003014 A2 | 1/2006 |
| WO | 2006031922 A2 | 3/2006 |
| WO | 2007035612 A2 | 3/2007 |
| WO | 2008051291 A2 | 5/2008 |
| WO | 2008140507 A2 | 11/2008 |
| WO | 2010120506 A2 | 10/2010 |
| WO | 2010148007 A2 | 12/2010 |

OTHER PUBLICATIONS

Office Action (Mail Date May 23, 2012) for U.S. Appl. No. 12/816,287, filed Jun. 15, 2010.
Office Action (Mail Date Apr. 11, 2013) for U.S. Appl. No. 12/816,287, filed Jun. 15, 2010.
Office Action (Mail Date Oct. 24, 2013) for U.S. Appl. No. 12/816,287, filed Jun. 15, 2010.
Office Action (Mail Date May 8, 2014) for U.S. Appl. No. 12/816,287, filed Jun. 15, 2010.
Office Action (Mail Date Apr. 29, 2013) for U.S. Appl. No. 13/345,194, filed Jan. 6, 2012.
Office Action (Mail Date Oct. 15, 2013) for U.S. Appl. No. 13/345,194, filed Jan. 6, 2012.
Notice of Allowance (Mail Date Feb. 6, 2014) for U.S. Appl. No. 13/345,194, filed Jan. 6, 2012.
Office Action (Mail Date Jul. 13, 2012) for U.S. Appl. No. 12/751,375, filed Mar. 31, 2010.
Office Action (Mail Date Apr. 12, 2013) for U.S. Appl. No. 12/751,375, filed Mar. 31, 2010.
U.S. Appl. No. 14/184,889, filed Feb. 20, 2014.
U.S. Appl. No. 14/185,010, filed Feb. 20, 2014.
Office Action (Mail Date Oct. 16, 2014) for U.S. Appl. No. 12/644,493, filed Dec. 22, 2009.
Bergers et al., "Modes of resistance to anti-angiogenic therapy", Nat. Rev. Cancer, 8(8):592-603 (2008) 23 pages.
Bergh et al., "Integrin $\alpha\beta3$ contains a cell surface receptor site for thyroid hormone that is linked to activation of mitogen-activated protein kinase and induction of angiogenesis", Endocrinology, 146(7):2864-2871 (2005) 8 pages.
Bergstrom et al., "Iodine-123 labelled Z-(R,R)-IQNP: a potential radioligand for visualization of M1 and M2 muscarinic acetylcholine receptors in Alzheimer's disease", Eur. J. Nucl. Med., 26(11):1482-1485 (1999).
Bergstrom et al., "Reduction of fibrinogen absorption on PEG-coated polystyrene surfaces", J. Biomed. Mat. Res., 26:779-790 (1992) 12 pages.
Beum et al., "Binding of Rituximab, Trastuzumab, Cetuximab, or mAb T101 to Cancer Cells Promotes Trogocytosis Mediated by THP-1 Cells and Monocytes", J. Immunol., 181:8120-8132 (2008) 13 pages.
Bhat et al., "NCAM-180, the largest component of the neural cell adhesion molecule, is reduced in dysmyelinating quaking mutant mouse brain", Brain Res., 452:373-377 (1988) 5 pages.
Bilello et al., "Effect of 2', 3'-Didehydro-3'-Deoxythymidine in an In Vitro Hollow-Fiber Pharmacodynamic Model System Correlates with Results of Dose-Ranging Clinical Studies", Antimicrob Agents Chemother., 38(6):1386-1391 (1994) 6 pages.
Blaszczyk-Thurin et al., "An Experimental Vaccine Expressing Wild-Type p53 induces Protective Immunity Against Glioblastoma Cells with High Levels of Endogenous p53", Scand. J. Immunol., 56:361-375 (2002) 15 pages.
Blight, A.R., "Macrophages and Inflammatory Damage in Spinal Cord Injury", J. Neurotrauma, 9(Suppl. 1):S83-S91 (1992) 10 pages.
Blood et al., "Tumor interactions with the vasculature: angiogenesis and tumor metastasis", Bioch. Biophys. Acta, 1032:89-118 (1990) 30 pages.
Bokemeyer et al., "Fluorouracil, Leucovorin, and Oxaliplatin With and Without Cetuximab in the First-Line Treatment of Metastatic Colorectal Cancer", J. Clin. Oncol., 27(5):663-671 (2009) 9 pages.
Bornebroek et al., "Potential for imaging cerebral amyloid deposits using 123I-labelled serum amyloid P component and SPET", Cucl. Med. Commun., 17:929-933 (1996) 6 pages.
Bozarth et al., "An improved method for the quantitation of cellular migration: Rose of $\alpha\beta3$ integrin in endothelial and smooth muscle cell migration", Meth. Cell Sci., 19(3):179-187 (1997) 9 pages.
Brachmann et al., "The SIR2 gene family, conserved from bacteria to humans, functions in silencing, cell cycle progression, and chromosome stability", Genes Dev. 9:2888-2902 (1995) 15 pages.
Braughler et al., "Involvement of Lipid Peroxidation in CNS Injury", J. Neurotrauma, 9(Suppl. 1):S1-S7 (1992) 8 pages.
Breier et al., "The role of vascular endothelial growth factor in blood vessel formation", Trends in Cell Biol., 6:454_456 (1996) 3 pages.
Bridoux et al., "Semisynthesis and pharmacological activities of Tetrac analogs: Angiogenesis modulators", Bioorg. Med. Chem. Lett., 19:3259-3263 (2009) 5 pages.
Bridoux et al., "Semisynthesis and pharmacological activities of thyroxine analogs: Development of new angiogenesis modulators", Bioorg. Med. Chem. Lett., 20(11):3394-3398 (2010) 5 pages.
Brockhoff et al., "Differential impact of Cetuximab, Pertuzumab and Trastuzumab on BT474 and SK-BR-3 breast cancer proliferation", Cell Prolif., 40:488-507 (2007) 20 pages.

(56) References Cited

OTHER PUBLICATIONS

Brooks et al., "Antintegrin αβ3 blocks human breast cancer growth and angiogenesis in human skin", J. Clin. Invest., 96(4):1815-1822 (1995) 8 pages.
Bulitta et al., "Development and Qualification of a Pharmacodynamic Model for the Pronounced Inoculum Effect of Ceftazidime against Pseudomonas aeruginosa", Antimicrob. Agents Chemother., 53(1):46-56 (2009) 11 pages.
Burgman et al., "Effect of Inhibitors of Poly(ADP-Ribose)Polymerase on the Radiation Resposne of HeLa S3 Cells", Radiat. Res., 119:380-386 (1989) 7 pages.
Carmeliet et al., "Molecular Basis of Angiogenesis Role of VEGF and VE-Cadherin", Ann. N.Y. Acad. Sci., 902:249-264 (2000) 16 pages.
Chanoine et al., "The role of transthyretin in the transport of thyroid hormone to cerebrospinal fluid and brain", Acta Medica Austriaca, 19(Suppl. 1):25-28 (19920) 5 pages.
Charness et al., "Ethanol Increases the Expression of Functional Delta-Opioid Receptors in Neurblastoma x Glioma NG108-15 Hybrid Cells", J. Biol. Chem., 261(7):3164-3169 (1986) 6 pages.
Charo et al., "The Vitronectin Receptor αβ3 Binds Fibronectin and Acts in Concert with α5β1 in Promoting Cellular Attachment and Spreading on Fibronectin", J. Cell Biol., 111(6 Pt. 1): 2795-2800 (1990) 6 pages.
Chase et al., "Principles of Radioisotope Methodology", 2nd Ed., Minneapolis, MN. Burgess Publ. Co., 1962, pp. 68, 87-90. 7 pages.
Chavakis et al., "Kinetics of integrin expression in the mouse model of proliferative retinopathy and success of secondary intervention with cyclic RGD peptides", Diabetologia, 45:262-267 (2002) 6 pages.
Cheng et al., "Molecular Aspects of Thyroid Hormone Actions", Endocri. Rev., 31(2): 139-170 (2010) 32 pages.
Cheresh et al., "Biosynthetic and Functional Properties of an Arg-Gly-Asp-directed Receptor Involved in Human Melanoma Cell Attachment to Vitronectin, Fibrinogen and von Willibrand Factor", J. Biol. Chem., 262(36):17703-17711 (1987) 9 pages.
Cheresh, D.A., "Human endothelial cells synthesize and express an Arg-Gly-Asp-directed adhesion receptor involved in attachment to fibrinogen and von Willibrand factor", Proc. Natl. Acad. Sci. U.S.A., 84:6471-6475 (1987) 9 pages.
Chiaguri et al., "Anoikis: A necessary death program for anchorage-dependent cells", Biochem. Pharmacol., 76:1352-1364 (2008) 13 pages.
Chinese Office Action for Application No. 2004800331846 dated Mar. 5, 2010 7 pages.
Chinese Office Action for Application No. 2004800331846, mailed Nov. 30, 2007, cited CN 1126589. 6 pages.
Clifton et al., "Marked Protection by Moderate Hypothermia After Experimental Traumatic Brain Injury", J. Cereb. Blood Flow Metab., 11(1):114-121 (1991) 9 pages.
Cody et al., "Molecular modeling of the thyroid hormone interactions with αβ3 integrin", Steriods, 72:165-170 (2007) 6 pages.
Cohen-Jonathan et al., "Radioresistance Induced by the High Molecular Forms of the Basic Fibroblast Growth Factor Is Associated with an increased G2 Delay and a Hyperphosphorylation of p34CDC2 in HeLa Cells", Cancer Res., 57:1364-1370 (1997) 7 pages.
Cohen-Jonathan et al., "αβ3 integrin pathway controls glioma radioresistance through ILK", Proc. Amer. Assoc. Cancer Res., 47:5180 (2006) (Abstract Only) 2 pages.
Cox et al., "The repair of potentially lethal damage in X-irradiated cultures of normal and ataxia telangiectasia human fibroblasts", Int. J. Radiat. Biol., 39(4):357-365 (1981) 9 pages.
Cristofanilli et al., "Thyroid Hormone and Breast Carcinoma. Primary Hypothyroidism is Associated with a Reduced Incidence of Primary Breast Carcinoma", Cancer, 103(6):1122-1128 (2005) 7 pages.
D'Arezzo et al., "Rapid Nongenomic Effects of 3,5,3'-Triiodo-L Thyronine on the Intracellular pH of L-6 Myoblasts are Mediated by Intracellular Calcium Mobilization and Kinase Pathways", Endocrinol., 145(12):5694-5703 (2004) 10 pages.
Database BIOSIS [Online], Accession No. PREV20040016159, Abstract, Mousa et al., "Discovery of pro-angiogenic effects of thyroid hormone and analogs", Blood, 102(11):77b-78b (2003) 1 page.
Davis et al., "Acting via a Cell Surface Receptor, Thyroid Hormone is a Growth Factor for Glioma cells," Cancer Res., 66(14):7270-7275 (2006) 6 pages.
Davis et al., "Cell-surface receptor for thyroid hormone and tumor cell proliferation", Expert Reviews in Endicrinology and Metabolism, 1(6):753-761 (2006) 10 pages.
Davis et al., "Mechanisms of nongenomic actions of thyroid hormone", Frontiers Neuroendocrinol., 29:211-218 (2008) 8 pages.
Davis et al., "Proangiogenic Action of Thyroid Hormone is Fibroblast Growth Factor-Dependent and is initiated at the Cell Surface." Cir. Res., 94(2004):1500-1506 7 pages.
Davis et al., "Promotion by thyroid hormone of cytoplasm-to-nucleus shutting of thyroid hormone receptors", Steroids, 73:1013-1017 (2008) 5 pages.
Davis et al., "Thyroxine Promotes Association of Mitogen-activated Protein Kinase and Nuclear Thyroid Hormone Receptor (TR) and Causes Serine Phosphorylation of TR", J. Biol. Chem., 275(48):38032-38039 (2000) 8 pages.
Davis et al., "Translational implications of nongenomic actions of thyroid hormone initiated at its integrin receptor", Am. J. Physiol. Endocrinol. Metab., 297:E1238-E1246 (2009) 9 pages.
De la Cruz et al., "Effect of Aspirin Plus Dipyridamole on the Retinal Vascular Pattern in Experimental Diabetes Mellitus", J. Pharmacol. Exp. Ther., 280(1):454-459 (1997) 6 pages.
Deardorff, D.L., "Isotonic Solutions", in Remington's Pharmaceutical Sciences, 15th Ed., Chapter 79, pp. 1405-1412, Mack Publishing Co., Easton (1975) 10 pages.
DeFesi et al., "3,5,3'-Triiodothyronine Effects on the Growth Rate and Cell Cycle of Cultured GC Cells", Endocrinol., 108(1):259-267(1981) 9 pages.
Demediuk et al., "Traumatic Spinal Cord Injury in Rats Causes Increases in Tissue Thromboxane But Not Peptidoleukotrienes", J. Neurosci. Res., 20:115-121 (1988) 7 pages.
DeRyck et al., "Neocortical localization of tactile/proprioceptive limb placing reactions in the rat", Brain Res., 573(1):44-60 (1992) 18 pages.
Di Chiro et al., "Glucose utilization of cerebral gliomas measured by [18F] fluorodeoxyglucose and positron emission tomography", Neurology, 32(12):1323-1329 (1982) 8 pages.
Dietrich et al., "Post-traumatic brain hypothermia reduces histopathological damage following concussive brain injury in the rat", Acta Neuropathol., 87(3):250-258 (1994) 10 pages.
Ding et al., "Radioprotection of Hematopoietic Tissue by Fibroblast Growth Factors in Fractionated Radiation Experiments", Acta Onocol., 36(3):337-340 (1997) 4 pages.
Dixon et al., "A fluid percussion model of experimental brain injury in the rat", J. Neurosurg., 67(1):110-119 (1987) 11 pages.
Drusano et al., "Pharmacodynamics of Abacavir in an In Vitro Hollow-Fiber Model System", Antimicrob. Agents Chemother., 46(2):464-470 (2002) 7 pages.
Dupont et al., "Antiangiogenic and antimetastatic properties of Neovastat (•-941), an orally active extract derived from cartilage tissue", Clin. Experim. Metastasis, 19:145-153 (2002) 9 pages.
Edwards et al., "Trypsinized BHK21 cells aggregate in the presence of metabolic inhibitors and in the absence of divalent cations", J. Cell Sci., 19(3):653-667 (1975) 16 pages.
Elkind et al., "Radiation Response of Mammalian Cells Grown in Culture. 1. Repair of X-Ray Damage in Surviving Chinese Hamster Cells", Radiat. Res., 13:556-593 (1960) 38 pages.
Elvin et al., "Cell Adhesiveness and the Cell Cycle: Correlation in Synchronized Balb/c 3T3 Cells", Biol. Cell, 48:1-10 (1983) 10 pages.
Ely and Berne, "Protective Effects of Adenosine in Myocardial Ischemia", Circulation, 85:893-904 (1992) 13 pages.
Ethier et al., "Adenosine stimulates proliferation of human endothelial cells in culture", Am. J. Physiol., 265:H131-H138 (1993) 8 pages.

(56) References Cited

OTHER PUBLICATIONS

Everts et al., "Uptake of 3,3',5.5'-Tetraiodothyroacetic Acid and 3,3',5'-Triiodothyronine in Cultured Rat Anterior Pituitary Cells and Their Effects on Thyrotropin Secretion", Endocrinol., 136(10):4454-4461 (1995) 8 pages.
Faden et al., "Endogenous Opioid Immunoreactivity in Rat Spinal Cord Following Traumatic Injury", Ann. Neurol., 17(4):386-390 (1985) 5 pages.
Faden, A.I., "Experimental Neurobiology of Central Nervous System Trauma", Crit. Rev. Neurobiol., 7(3/4):175-186 (1993) 13 pages.
Feeney et al., "Amphetamine, Haloperidol, and Experience Interact to Affect Rate of Recovery After Motor Cortex Injury", Science, 217(4562):855-857 (1982) 4 pages.
Fei et al., "P53 and radiation responses", Oncogene, 22:5774-5783 (2003) 10 pages.
Felding-Habermann et al., "Integrin activation controls metastasis in human breast cancer", Proc. Natl. Acad. Sci. U.S.A., 98(4):1853-1858 (2001) 6 pages.
Feng et al., "Fibrin and Collagen Differentially Regulate Human Dermal Microfascular Endothelial Cell Integrins: Stablization of $\alpha/\beta 3$ mRNA by Fibrin", J. Invest. Dermatol., 113(6):913-919 (1999) 7 pages.
Fife et al., "Effects of tetracyclines on angiogenesis in vitro", Cancer Letters, 153:75-78 (2000) 4 pages.
Folkman, J., "Angiogenesis in cancer, vascular, rheumatoid and other disease", Nat. Med., 1(1):27-31 (1995) 5 pages.
Freese et al., "Characterization and mechanism of glutamate neurotoxicity in primary striatal cultures", Brain Res., 521(1/2):254-264 (1990) 12 pages.
Frye, R.A., "Characterization of Five Human cDNAs with Homonology to the Yeast SIR2. Gene: Sir2-like Proteins (Sirtuins) Metabolize NAD and May Have Protein ADP-Ribosyltransferase Activity", Biochem. Biophys. Res. Comm., 260:273-279 (1999) 7 pages.
Fujii et al., "Crystal Structure of Trimestatin, a Disintegrin Containing a Cell Adhesion Recognition Motif RGD", J. Mol. Biol., 332:1115-1122 (2003) 8 pages.
Gavrieli et al., "Identification of Programmed Cell Death In Situ via Specific Labeling of Nuclear DNA Fragmentation", J. Cell. Biol., 119(3):493-501 (1992) 9 pages.
GenBank Accession No. AF083106, Apr. 14, 2000 5 pages.
GenBank Accession No. AF083107, Mar. 21, 2001. 3 pages.
GenBank Accession No. NM_002210, Jun. 15, 2008 8 pages.
GenBank Accession No. NM_012238, Apr. 25, 2010. 8 pages.
GenBank Accession No. NM_030593, Mar. 14, 2010. 8 pages.
GenBank Accession No. NP_036370, Apr. 25, 2010. 6 pages.
GenBank Accession No. NP_501912, Nov. 13, 2008. 4 pages.
GenBank Accession No. P53685, Apr. 20, 2010. 8 pages.
Geng et al., "A Specific Antagonist of the p110σ Catalytic Component of Phosphatidylinositol 3'-Kinase, IC486068, Enchances Radiation-Induced Tumor Vascular Destruction", Cancer Res., 64:4893-4899 (2004) 7 pages.
Ginis et al., "Hypoxia affects tumor cell invasiveness in vitro: the role of hypoxia-activated ligand HAL 1/13 (Ku 86 autoantigen)", Cancer Lett., 154:163-174 (2000) 12 pages.
Gladson, C.L., "Expression of integrin αβ3 in Small Blood Vessels of Giioblastoma Tumors", J. Neurpath. Exp. Neurol., 55(11):1143-1149(1996) 7 pages.
Glinskii et al., "Modification of survival pathway gene expression in human breast cancer cells by tetraiodothyroacetic acid (tetrac)", Cell Cycle, 8(21):3562-3570 (2009) 9 pages.
Glinsky et al., "Classification of Human Breast Cancer Using Gene Expression Profiling as a Component of the Survival Predictor Algorithm", Clin. Cancer Res., 10:2272-2283 (2004) 12 pages.
Glinsky et al., "Gene expression prfiling predicts clinical outcome of prostate cancer", J. Clin. Invest., 113(6):913-923 (2004) 11 pages.
Glinsky et al., "Microarray analysis identifies a death-from-cancer signature predicting therapy failure in patients with multiple types of cancer", J. Clin. Invest., 115(6):1503-1521 (2005) 19 pages.
Glinsky et al., "Microarray Analysis of Xenograft-Derived Cancer Cells Lines Representing Multiple Experimental Models of Human Prostate Cancer", Mol. Carcinog., 37:209-221 (2003) 13 pages.
Goldstein et al., "Influence of Lesion Size and Location on Amphetamine-Facilitated Recovery of Beam-Walking in Rats", Behav. Neurosci., 104(2):320-327 (1990) 9 pages.
Goldstein, A., "Estimating the Error Variance and the Confidence Interval for a Regression Line", in Biostatistics, The MacMillan Co., New York, pp. 139-146 (1964) 10 pages.
Goodman, M.M., "Automated Synthesis of Radiotracers for PET Applications", in Clinical Positron Emission Tomography, Mosby Yearbook, K.F. Hubner et al., Chapter 14, pp. 110-122 (1992) 13 pages.
Grant, D.B., "Monitoring TSH concentrations during treatment for gongenital hypothyroidism", Arch. Disease Childhood, 66:669-670 (1991) 2 pages.
Gregoriadis, "Liposomes", in Drug Carriers in Biology and Medicine, Chapter 14, pp. 287-341, Academic Press (1979) 57 pages.
Guigon et al., "Regulation β-Catenin by a Novel Nongenomic Action of Thyroid Hormone β Receptor", Mol. Cell. Biol., 28(14):4598-4608 (2008) 11 pages.
Hahn et al., "Plateau-phase cultures of mammalian cells: An in vitro model for human cancer", Curr. Top. Radiat. Res. Q., 8:39-83 (1972) 45 pages.
Halks-Miller et al., "CCR1 Immunoreactivity in Alzheimer's Disease Brains", Society for Neuroscience Meeting, Abstract #787.6, vol. 24 (1998) Abstract Only. 1 page.
Hansebout, R.R., "A Comprehensive Review of Methods of Improving Cord Recovery After Acute Spinla Cord Injury", in Early Management of Acute Spinal Cord Injury, pp. 181-196 (1982) 16 pages.
Hartert, H., "Blutgerinnungsstud Mit Der Thrombelastogeraphie, Einem Neuen Untersuchungsverfahren", Klinische Wochenschrift 26(37/38):577-583 (1948) German Language Only. 9 pages.
Hashimoto et al., "Matrix Metalloproteinases Cleave Connective Tissue Growth Factor Reactivate Angiogenic Activity of Vascular Endothelial Growth Factor 165", J. Biol. Chem. 277(39):36288-36295 (2002) 8 pages.
Heller et al., "Inhibition of potentially lethal damage recovery by altered pH, glucose utilization and proliferation in plateau growth phase human glioma cells", Int. J. Radiat. Biol., 66(1):41-47 (1994) 7 pages.
Hercbergs et al., "GL261 brain tumor cells: responses to signle or fractionated x-irradiation with the αβ3 integrin tyroxine receptor antagonist tetrac (tetraiodothyroacetic acid)", 20th EORTC-NCI-AACR Symposium on Molecular Targets and Cancer Therapeutics, Geneva, Switzerland, Oct. 2008. 304 pages.
Hercbergs et al., "GL261 brain tumor cells: responses to single or fractionated x-irradiation with the αβ3 integrin tyroxine receptor antagonist tetrac (tetraiodothyroacetic acid)", Euro. J. Cancer, 6(12):172 (Abstract Only) 4 pages.
Hercbergs et al., "Propylthiouracil-induced Chemical Hypothyroidism with High-Dose Tamoxifen Prolongs Survival in Recurrent High Grade Ciioma: A Phase I/II Study", Anticancer Res., 23:617-626 (2003) 10 pages.
Hercbergs, A., "The Thyroid Gland as an Intrinsic Biologic Response-Modifier in Advanced Neoplasia—A Novel Paradigm", in vivo, 10:245-247 (1996) 3 pages.
Hercbergs, et al., GL261 Brain Tumor Cells: In Vitro Single and Fractionated Dose Responses to X-Rays and Modification by Tetrac (Tetraiodothyroacetic Acid), The Cleveland Clinic Foundation, Department of Radiation Oncology 46 pages.
Hercbergs, et al., "Radiosensitization of GL261 glioma cells by tetraiodothyroacetic acid (tetrac)", Cell Cycle, 8(16):2586-2591 (2009) 6 pages.
Hermanson, "Modification with Synthetic Polymers", in Bioconjugate Tech., Ch. 15, Academic Press, San Diego, CA, pp. 617-618 (1996) 4 pages.
Hoff et al., "Medullary Thyroid Carcinoma", Hematol. Oncol. Cin. North Am., 21(3):475-488 (2007) 14 pages.
Horuk et al., "Expression of Chemokine Receptors by Subsets of Neurons in the Central Nervous System", J. Immunol., 158:2882-2890 (1997) 9 pages.

(56) References Cited

OTHER PUBLICATIONS

Hubner, K.F., "University of Tennessee Biomedical Imaging Center and Transfer of Technology to the Clinical Floor", in Clinical Positron Emission Tomography, Mosby Yearbook, K.F. Hubner et al., Chapter 2, pp. 4-16 (1992) 13 pages.
Hudlicka et al., "Factors involved in capillary growth in the heart", Mol. Cell. Biochem, 147:57-68 (1995) 12 pages.
Igarashi et al., "Techniques Supporting Angiogenesis Therapy 2: DDS Technique Supporting Regenerative Medicine." Inflamm. Immun. 10.6(2002):652-658 7 pages.
Illario et al., "Fibronectin-Induced Proliferation in Thyroid Cells is Mediated by αβ3 Integrin through Ras/Raf-1/MEK/ERK and Calcium/CaMKII Signals", J. Clin. Endocrinol. Metab., 90(5):2865-2873 (2005) 9 pages.
Ingerman-Wojenski et al., "Evaluation of electrical aggregometry: comparison with optial aggregometry, secretion of ATP, and accumulation of radiolabeled platelets", J. Lab. Clin. Med., 101(1):44-52 (1983) 10 pages.
Iwata et al., "A new, convenient method for the preparation of 4-[18F]fluorobenzyl halides", Applied Radiation and Isotopes, 52(1):87-92 (2000) 7 pages.
Jain, K.K., "Strategies and technologies for drug delivery systems", TIPS, 19:155-157 (1998) 5 pages.
Janssen et al., "Pathogenesis of Spinal Cord Injury and Newer Treatments—A Review", Spine, 14(1):23-32 (1989) 11 pages.
Jeffrey et al., "The preparation and characterisation of poly(lactide-co-glycolide) microparticles. 1. Oil-in-water emulsion solvent evaporation", Int. J. Pharm., 77:169-175 (1991) 7 pages.
Jonker et al., "Cetuximab for the Treatment of Colorectal Cancer", N. Engl. J. Med., 357(20):2040-2048 (2007) 9 pages.
Jordan et al., "Thyroid Status is a Key Modulator of Tumor Oxygenation: Implication for Radiation Therapy", Radiat. Res., 168:428-432 (2007) 5 pages.
Kalofonos et al., "Monoclonal Antibodies in the Management of Solid Tumors", Curr. Top. Med. Chem., 6:1687-1705 (2006) 19 pages.
Kapiszewska et al., "The Effects of Reduced Temperature and/or Starvation Conditions on the Radiosensitivity and Repair of Potentially Lethal Damage and Sublethal Damage in L5178Y-R and L5178Y-S Cells", Radiat. Res., 113:458-472 (1988) 15 pages.
Kastan et al., "A Mammalian Cell Cycle Checkpoint Pathway Utlizing P53 and GADD45 is Defective in Ataxia-Telangiectasia", Cell. 71:587-597 (1992) 11 pages.
Kawasuji et al., Jap. Circ. J., 63(Suppl. 1):65 (1999) Japanese Abstract Only. 3 pages.
Kerr et al., "Novel Small Molecule α Integrin Antagonists: Comparative Anti-Cancer Efficacy with Known Angiogenesis Inhibitors", Anticancer Res., 19:959-968 (1999).
Kerr et al., "Small molecule α integrin antagonists: novel anticancer agents", Exp. Opin. Invest. Drugs, 9(6):1271-1279 (2000) 9 pages.
Kim et al., "Regulation of Antiogenesis in Vivo, by Ligation of Integrin α5β1 with the Central Cell-Binding Domaing of Fibronectin", Am. J. Pathol., 156(4): 1345-1362 (2000) 18 pages.
Kim et al., "Soluble Flt-1 gene delivery using PEI-g-PEG-RGD conjugate for anti-angiogenesis", J. Control Release, 106:224-234 (2005) 11 pages.
Kimelberg, H.K., "Astrocytic Edema in CNS Trauma", J. Neurotrauma, 9(Suppl. 1):S71-S81 (1992) 12 pages.
Kitevska et al., "Caspase-2: controversial killer or checkpoint controller?", Apoptosis, 14:829-848(2009) 20 pages.
Kleczkowska et al., "Differntial poly(ADP-ribose) metabolism in repair-proficient and repair-deficient murine lymphoma cells", Mut. Res., 235:93-99 (1990) 7 pages.
Klunk et al., "Development of Small Molecule Probes for the Beta-Amyloid Protein of Alzheimer's Disease", Neurobiol. Aging, 15(6):691-698 (1994) 8 pages.
Kobayashi et al., "Drug Delivery Catheter." Surg. Front. 9.1(2002):55-57 3 pages.
Konno et al., "Antiogenetic therapy for carcinoma", Igaku No Ayumi, 194(10): 824-828 (2000) 5 pages.
Koutras et al., "Antiproliferative effect of exemestane in lung cancer cells", Mol. Cancer, 8(1):109 (2009) 12 pages.
Koyama et al., "Recent Status and Future Perspectives in Therapeutic Angiogenesis", Prog. Med., 22(12):3070-3076 (2002) (English Abstract) 7 pages.
Kramer et al., "Human Microvascular Endothelial Cells Use β1 and β3 Integrin Receptor Complexes to Attach to Laminin", J. Cell Biol., 111:1233-1343 (1990) 11 pages.
Kumar et al., "Enhancing Effect of Thyroxine on Tumor Growth and Metastases in Syngeneic Mouse Tumor Systems", Cancer Res., 39:3515-3518 (1979) 4 pages.
Kuroki et al., "Diabetic retinopathy—The mechanisms of the ocular neovascularization of the development of anti-angiogenic drugs-", Nippon Rinsho, 57(3):584-589 (1999) (English Abstract Only) 6 pages.
Kwok et al., "Differences in EGF rated radiosensitisation of human squamous carcinoma cells with high and low numbers of EGF receptors", Br. J. Cancer, 64:251-254 (1991) 4 pages.
Lameloise et al., "Differences between the effects of thyroxine and tetraiodothyroacetic acid on TSH suppression and cardiac hypertrophy", Eur. J. Endocrinol., 144:145-154 (2001) 10 pages.
Lawler et al., "Cell Attachment to Thombospondin: The Role of ARG-GLY-ASP, Calcium and Integrn Receptors", J. Cell Biol., 107(6 Pt. 1): 2351-2361 (1988) 11 pages.
Letterio et al., "Maternal Rescue of Transforming Growth Facotr-β1 Null Mice", Science, 264:1936-1938 (1994) 4 pages.
Li et al., "Requirement of hypoxia-inducible factor-1α down-regulation in mediating the antitumor activity of the anit-epidermal growth factor receptor monoclonal antibody cetuximab", Mol. Cancer Ther., 7(5):1207-1217 (2008) 11 pages.
Lin et al., "Androgen-induced human breast cancer cell proliferation is mediated by discrete mechanisms in estrogen receptor-α-positive and -negative breast cancer cells", J. Steroid Biochem. Mol. Biol., 113:182-188 (2009) 7 pages.
Lin et al., "Identification of the Putative MAP Kinase Docking Site in the Thyroid Hormone Receptor-β1 DNA-Binding Domain: Functional Consequences of Mutations at the Docking Site", Biochem., 42:7571-7579 (2003) 9 pages.
Lin et al., "Integrin αβ3 contains a receptor site for resveratrol", FASEB J., 20(10): 1742-1744 (2006) 3 pages.
Lin et al., "L-Thyroxine vs. 3,5,3'-triiodo-L-thyronine and cell proliferation: activation of mitogen-activated protein kinase and phosphatidylinositol 3-kinase", Am. J. Physiol. Cell Physiol., 296:C980-C991 (2009) 12 pages.
Lin et al., "Resveratrol Causes COX-2- and p53-Dependent Apoptosis in Head and Neck Squamos Cell Cancer Cells", J. Cell Biochem., 104:2131-2142 (2008) 12 pages.
Lin et al., "Resveratrol Induced Serine Phosphorylation of p53 Causes Apoptosis in a Mutant p53 Prostate Cancer Cell Line", J. Urol., 168:748-755 (2002) 8 pages.
Lin et al., "Resveratrol is pro-apoptotic and thyroid hormone is anti-apoptotic in glioma cells: both actions are integrin and ERK mediated", Carcinogenesis, 29(1):62-69 (2008) 8 pages.
Lin et al., "The pro-apoptotic action of stilbene-induced COX-2 in cancer cells: Convergence with the anti-apoptotic effect of thyroid hormone", Cell Cycle, 8(12):1877-1882 (2009) 6 pages.
Lin et al., "Thyroid hormone is a MAPK-dependent growth factor for thyroid cancer cells and is anti-apoptotic", Steriods, 72:180-187 (2007) 8 pages.
Liu et al., "Calcineurin Is a Common Target of Cyclophilin-Cyclosporin A and FKBP-FK506 Complexes", Cell, 66:807-815 (1991) 9 pages.
Lorger et al., "Activation of tumor cell integrin αβ3 controls angiogenesis and metastatic growth in the brain", Proc. Natl. Acad. Sci. U.S.A., 106(26):10666-10671 (2009) 7 pages.
Louie et al., "Pharmacodynamics of Levofloxacin in a Murine Pneumonia Model of Pseudomonas aeruginosa Infection: Determination of Epithelial Lining Fluid Targets", Antimicrob Agents Chemother., 53(8):3325-3330 (2009) 6 pages.
Luidens et al., "Thyroid hormone and angiogenesis", Vascular Pharmacology, 52(3-4):142-145 (2010) 4 pages.

(56) References Cited

OTHER PUBLICATIONS

Lyons et al., "The Expression of an N-CAM Serum Fragment is Positively Correlated with Severity of Negative Featues in Type II Schizophrenia", Biol. Psychiatry, 23:769-775 (1988) 7 pages.

Ma, et al., "Use of Encapsulated Single Chain Antibodies for Induction of Anti-Idiotypic Humoral and Cellular Immune Responses", J. Pharm. Sci., 87:1375-1378 (1998). 4 pages.

Mahmood et al., "An N2S2 Teradentate Chelate for Solid-Phase Synthesis: Evaluation in Solution and Solid Phase and Characterization of Technetium-99 Complexes", Technetium, Rhenium and Other Metals in Chemistry and Nuclear Medicine, 5:71-76 (1999) 6 pages.

Mandelin et al., "Extracellular and Intracellular Mechanisms That Mediate the Metastatic Activity of Exogenous Osteopontin", Cancer, 115:1753-1764 (2009) 12 pages.

Mangale et al., "Identification of genes regulated by an interaction between αβ3 integrin and vitronectin in murine decidua", Reprod. Fertil. Dev., 20:311-319 (2008) 10 pages.

Markgraf et al., "Sensorimotor and cognitive consequences of middle cerebral artery occlusion in rates", Brain Res., 575(2):238-246 (1992) 10 pages.

Martens et al., "Inhibition of Glioblastoma Growth in a Highly Invasive Nude Mouse Model Can Be Achieved by Targeting Epidermal Growth Factor Receptor but not Vascular Endothelial Growth Factor Receptor-2", Clin. Cancer Res., 14(17):5447-5458 (2008) 12 pages.

Masson-Gadais et al., "Integrin αβ3 requirement for VEGFR2-mediated activation of SAPK2/p38 and Hsp90-dependent phosphorylation of focal adhesion kinase in endothelial cells activated by VEGF", Cell Stress Chaperones, 8(1):37-52 (2003) 16 pages.

McCarty et al., "Promises and Pitfalls of Anti-Angiogenic Therapy in Clinical Trials." Trends Mol. Med. 9.2(2003):53-58 6 pages.

Meneses et al., "Recombinant angiostatin prevents retinal neovascularization in a murine proliferative retinopathy model", Gene Therapy, 8(8):646-648 (2011) 3 pages.

Mezosi et al., "Nongenomic effect of thyroid hormone on free-radical production in human polymorphonuclear leukocytes", J. Endocrinol., 185:121-129 (2005) 9 pages.

Mishkin et al., "Increased Survival of Rats Bearing Morris Hepatoma 7800 after Induction of Hypothroidism", Cancer Res., 39:2371-2375 (1979) 5 pages.

Miyaguchi et al., "Correlation of Epidermal Growth Factor Receptor and Radiosensitivity in Human Maxillary Carcinoma Cell Lines", ActaOtolaryngol., 118:428-431 (1998) 4 pages.

Moeller et al., "Cytosolic Action of Thyroid Hormone Leads to Induction of Hypoxia-inducible Factor-1α and Glycolytic Genes", Molec. Endo., 19(12):2955-2963 (2005) 9 pages.

Moeller et al., "Thyroid hormone mediated changes in gene expression can be initiated by cytosolic action of the thyroid hormone receptor beta through the phosphatidylinositol 3-kinase pathway", Nuclear Receptor Signaling, 4:E020 (2006) 4 pages.

Mohamed et al., "Wound healing properties of cimetidine in vitro", Drug Intell. Clin. Pharm., 20(12):973-975 (1986) 4 pages.

Monferran et al., "αβ3 and αβ5 integrins control glioma cell response to ionising radiation through ILK and RhoB", Int. J. Cancer, 123:357-364 (2008) 8 pages.

Morand et al., "Effect of Iodide on Nicotinamide Adenine Dinucleotide Phosphate Oxidase Activity and Duox2 Protein Expression in Isolated Porcine Thyroid Follicles", Endo., 144(4):1241-1248 (2003) 8 pages.

Moreno et al., "Metabolic Effects of Thyroid Hormone Derivatives", Thyroid, 18(2):239-253 (2008) 15 pages.

Moreno et al., "Thyroid Economy—Regulation, Cell Biology, Thyroid Hormone Metabolism and Action: The Special Edition: Metabolic Effects of Thyroid Hormones. Metabolic Effects of Thyroid Hormone Derivatives", Thyroid, 18(2):239-253 (2008) 15 pages.

Mousa et al., "Cellular and Molecular Mechanisms of Nicotine's Pro-Angiogenesis Activity and Its Potential Impact on Cancer", J. Cell. Biochem., 97:1370-1378 (2006) 9 pages.

Mousa et al., "Discovery of Pro-Angiogenic Effects of Nicotine's Pro-Angiogenesis Activity and Its Potential Impact on Cancer", J. Cell. Biochem., 97:1370-1378 (2006) Abstract Only. 3 pages.

Mousa et al., "Proangiogenesis Action of the Thyroid Hormone Analog 3,5-Diiodothyropropionic Acid (DITPA) Is Initiated at the Cell Surface and is Integrin Mediated", Endocrinol., 147(4):1602-1607 (2006) 6 pages.

Mousa et al., "Pro-angiogenesis action of thyroid hormone and analogs in a three-dimensional in vitro microvascular endothelial sprouting model", Int. Angiol., 25(4):407-413 (2006) 7 pages.

Mousa et al., "Tetraiodothyroacetic (tetrac) inhibits angiogenesis", In: Program of the 77th Annual Meeting of the American Thyroid Association, Phoenix, AZ, 2006: Abstract 108. 4 pages.

Mousa et al., "Tetraiodothyroacetic acid, a small molecule integrin ligand, blocks angiogenesis induced by vascular endothelial growth factor and basic fibroblast growth factor", Angiogenesis, 11:183-190 (2008) 8 pages.

Mousa et al., "The Proangiogenic Action of Thyroid Hormone Analogue GC-1 Is Initiated at an Integrin", J. Cardiovasc. Pharmacol., 46(3):356-360 (2005) 6 pages.

Mousa, S.A., "Mechanisms of Angiogenesis: Potential Therapeutic Targets", in Angiogenesis Inhibotors and Stimulators: Potential Therapeutic Implications, Landes Bioscience, Georgetown, Texas, Chapter I, pp. 1-12 (2000) 14 pages.

Mousa, S.A., et al., "Effect of Resveratrol on Angiogenesis and Platelet/Fibrin-Accelerated Tumor Growth in the Chick Chorioallantoic Membrane Model," Nutr. Cancer, 52(1):59-65 (2005) 7 pages.

Muller et al., "The Double Life of the Ku Protein: Facing the DNA Breaks and the Extracellular Environment", Cell Cycle, 4(30:438-441 (2005) 4 pages.

Ndiaye et al., "Red wine polyphenol-induced, endothelium-dependent NO-mediated relaxation is due to the redox-sensitive PI3-kinase / Akt-dependent phosphorylation of endothelial NO-synthase in the isolated porcine coronary artery", FASEB J., 19(3):455-457 (2005) 3 pages.

Nehls et al., "A microcarrier-based concultivation system for the investigation of factors and cells involved in angiogenesis in three-dimensional fibrin matrices in vitro", Histochem. Cell Biol., 104(6):459-466 (1995) 8 pages.

Nehls et al., "A Novel Micrcarrier-Based in Vitro Assay for Rapid and Reliable Quantification of Three-Domensional Cell Migration and Angiogenesis", Microvasc. Res., 50(3):311-322 (1995) 12 pages.

Neises et al., "Esterification of Carboxylic Acids with Dicyclohexylcarbodiimide/4-Dimethylaminopyridine: tert-Butyl Ethyl Fumarate", Org. Synth., 7:93 (1990); 63:183 (1985) 3 pages.

Sunwoo et al., "Novel Proteasome Inhibitor PS-341 Inhibits Activation of Nuclear Factor-κB, Cell Survival, Tumor Growth, and Angiogenesis in Squamous Cell Carcinoma", Clin. Cancer Res., 7:1419-1428 (2001) 10 pages.

Szatmari et al., "Detailed characterization of the mouse glioma 261 tumor model for experimental glioblastoma therapy", Cancer Sci., 97(6):546-553 (2006) 8 pages.

Szumiel, I., "Ca2+, Mg2+ and (Adenosine Diphosphate Ribose)n in Cellular Response to Irradiation", J. Theor. Biol., 101:441-451 (1983) 11 pages.

Takemaru et al., "Chibby, a nuclear β-catenin-associated antagonist of the Wnt/Wingless pathway", Nature, 422:905-909 (2003) 5 pages.

Tanaka et al., J. Soc. Gastroenterological Surgery, 27(2):360 (1996) 3 pages.

Tang et al., "Resveratrol-induced Cyclooxygenase-2 facilitates p53-dependent apoptosis in human breast cancer cells", Mol. Cancer Ther., 5(8):2034-2042 (2006) 9 pages.

Tang et al., "Thyroid Hormone Causes Mitogen-Activated Protein Kinase-Dependent Phosphorylation of the Nuclear Estrogen Receptor", Endocrinol., 145(7):3265-3272 (2004) 8 pages.

Tator et al., "Review of the secondary injury theory of acute spinal cord trauma with emphasis on vascular mechanisms", J. Neurosurg., 75(1):15-26 (1991) 13 pages.

Theodossiou et al., "Propylthiouracil-induced Hypothyroidism Reduces Xenograft Tumor Growth in Athymic Nude Mice", Cancer, 86:1596-1601 (1999) 6 pages.

(56) References Cited

OTHER PUBLICATIONS

Thompson et al., "The Clinical Manipulation of Angiogenesis: Pathology, Side-Effects, Surprises, and Opportunites with Novel Human Therapies." J. Pathol. 190(2000):330-337 8 pages.

Thraves et al., "Radiosensitization of Human Fibroblasts by 3-Aminobenzamide: An Inhibitor of Poly(ADP-Ribosylation)", Radiat Res., 104:119-127 (1985) 9 pages.

Tol et al., "Chemotherapy, Bevacizumab, and Cetuximab in Metastatic Colorectal Cancer", N. Engl. J. Med., 360(6):563-572 (2009) 10 pages.

Tomanek et al., "A Thyroid Hormone Analog Stimulates Angiogenesis in the Post-infarcted Rat Heart", J. Mol. Cell Cardiol., 30(5):923-932 (1998) 10 pages.

Tomanek et al., "Angiogenesis: New Insights and Therapeutic Potential", Anatomical Record (New Anat.), 261:126-135 (2000) 10 pages.

Tomanek et al., "Early Coronary Angiogenesis in Resposne to Thyroxine: Growth Characteristics and Upregulation of Basic Fibroblast Growth Factor", Circ. Res., 82(5):587-593 (1998) 8 pages.

Tomanek et al., "Growth of the Coronary Vasculature in Hypertrophy: Mechanisms and Model Dependence", Cell. Mol. Bio. Res., 40(2):129-136 (1994) 8 pages.

Toms et al., "Thyroid Hormone Depletion Inhibits Astrocytoma Proliferation via a p53-Independent Induction of p21 (WAF/1CIP1)", Anticancer Res., 18:289-293 (1998) 5 pages.

Tuttle et al., "Recombinant Human TSH-Assisted Radioactive Iodine Remnant Ablation Achieves Short-Term Clinical Recurrence Rates Similar to Those of Traditional Thyroid Hormone Withdrawal", J. Nucl. Med., 49(5):764-770 (2008) 7 pages.

Tzirogiannis et al., "Enhanced Proliferation of Human Lung Adenocarcinoma and Small Cell Lung Carcinoma Cells Directed from the Cell Surface by Thyroid Hormone", in 89th Annual Meeting, The Endocrine Society (2007) Abstract Only 3 pages.

Utsumi et al., "Potentially Lethal Damage Versus Sublethal Damage: Independent Repair Processes in Actively Growing Chinese Hamster Cells", Radiat. Res., 77:346-360 (1979) 9 pages.

Van Waes et al., "Effects of the novel α integrin antagonist SM256 and cis-platinum on growth of murine squamos cell carcinoma PAM LY8", Int. J. Oncol., 16(6):1189-1195 (2000) 8 pages.

VanCutsem et al., "Cetuximab and Chemotherapy as Initial Treatment for Metastatic Colorectal Cancer", N. Engl. J. Med., 360:1408-1417 (2009) 10 pages.

Varnes et al., "The Effect of pH on Potentially Lethal Damage Recovery in A549 Cells", Radiat. Res., 108:80-90 (1986) 11 pages.

Velasco et al., "Dermatological Aspects of Angiogenesis." Brit. J. Dermatol. 147(2002):841-852 12 pages.

Wang et al., "DITPA stimulated bFGF, VEGF, angiopoietin, and Tie-2 and facilates coronary arteriolar growth", Am. J. Physiol. Heart Circ. Physiol., 284(2):H613-H618 (2003) 6 pages.

Wang et al., "Integrin-associated Protein Stimulates α2β1-dependent Chemotaxis via Gi-mediated inhibition of Adenylate Cyclase and Extracelular-regulated Kinases", J. Cell. Biol., 147:389-399 (1999) 11 pages.

Wen et al., "Prognostic Value of EGFR and TGF-α in Early Laryngeal Cancer Treated With Radiotherapy", Laryngoscope, 106(7):884-888 (1996) 6 pages.

Werdelin et al., "Neuropeptides and neural cell adhesion molecule (NCAM) in CSF from patients with ALS", Acta Neurol. Scand., 79(3):177-181 (1989).

Wilkinson, J.H., "Synthesis of some Possible Metabolites of Thyroxine and Triiodothyronine", Biochem. J., 63:601-605 (1956) 5 pages.

Xia et al., "Chemokines/chemokine receptors in the central nervous system and Alzheimer's disease", J. NeuroVirol., 5:32-41 (1999) 11 pages.

Yalcin et al., "Tetraidothyroacetic Acid (Tetrac) and Tetrac Nanoparticles Inhibit Growth of Human Renal Cell Carcinoma Xenografts", Anticancer Res., 29:3825-3832 (2009) 7 pages.

Yalcin et al., "Tetraiodothyroacetic Acid (Tetrac) and Nanoparticulate Tetrac Arrest Growth of Medullary Carcinoma of the Thyroid", J. Clin. Endocrinol. Metab., 95(4):1972-1980 (2010) 7 pages.

Yalcin et al., "Tetraiodothyroacetic Acid (Tetrac) and Nanoparticulate Tetrac Arrest Growth of Medullary Carcinoma of the Thyroid", J. Clin. Endocrinol. Metab., 95(4):1972-1980 (2010) 9 pages.

Yalcin et al., "Tetraiodothyroacetic Acid and Tetraiodothyroacetic Acid Nanoparticle Effectively Inhibit the Growth of Human Follicular Thyroid Cell Carcinoma", Thyroid, 20(3):281-286 (2010) 6 pages.

Yanase et al., "Role of N-methyl-D-aspartate receptor in acute spinal cord injury", J. Neurosurg., 83:884-888 (1995) 6 pages.

Yang et al., "Rab7b, a novel lysosome-associated small GTPase, is involved in monocytic differentiation of human acute promyelocytic leukemia cells", Biochem. Biophys. Res. Commun., 318:792-799 (2004) 8 pages.

Yang, et al., "Enhanced inhibition of adipogenesis and induction of apoptosis in 3T3-L1 adipocytes with combinations of resveratrol and quercetin", Life Sci., 82:1032-1039 (2008) 8 pages.

Yonkers et al., "Sensory Neuron Sodium Current Requires Nongenomic Actions of Thyroid Hormone During Development", J. Neurophysiol., 100:2719-2725 (2008) 7 pages.

Young, W., "Role of Calcium in Central Nervous System Injuries", J. Neurotrauma, 9(Suppl. 1): S9-S25 (1992) 18 pages.

Young, W., "Secondary injury mechanisms in acute spinal cord injury", J. Emerg. Med., 11:13-22 (1993) 11 pages.

Yu et al., "Osteopontin Gene is Expressed in the Dermal Papilla of Pelage Follicles in a Hair-Cycle-Dependent Manner", J. Invest. Dermatol., 117:1554-1558 (2001) 5 pages.

Yu, et al., "The Compressor Silencing Mediator for Retinoid and Thyroid Hormone Receptor Facilitates Cellular Recovery from DNA Double-Strand Breaks", Cancer Res., 66(18):9316-9322 (2006) 7 pages.

Zhang et al., "Oestrogen inhibits resveratrol-induced post-translational modification of p53 and apoptosis in breast cancer cells", Br. J. Cancer, 91:178-185 (2004) 8 pages.

Zhang et al., "Quantitative PET Imaging of Tumor Integrin αvβ3 Expression with 18F-FRGD2", J. Nucl. Med., 47:113-121 (2006) 9 pages.

Zhen et al., "Synthesis and Amyloid Binding Properties of Rhenium Compleses: Preliminary Progress Toward a Reagent for SPECT Imaging of Alzheimer's Disease Brain", J. Med. Chem., 42:2805-2815 (1999) 11 pages.

Zhuang et al., "99mTc-Labeled MIBG Derivatives: Novel 99m Tc Complexes as Myocardial Imaging Agents for Sympathetic Neurons", Bioconjugate Chem., 10:159-168 (1999) 10 pages.

Avgoustakis, et al., "PLGA-mPEG nanoparticles of cisplatin: in vitro nanoparticle degradation, in vitro drug release and in vivo drug residence in blood properties" J. Contr. Rel. 2002, 79, 123-135. 13 pages.

Newcomb et al., "Radiation Sensitivity of GL261 Murine Glioma Model and Enhanced Radiation Response by Flavopiridol", Cell Cycle., 5(1):93-99 (2006) 7 pages.

Nickoloff et al., "Aberrant Production of Interleukin-8 and Thrombospondin-1 by Psoriatic Keratinocytes Mediates Angiogenesis." Am. J. Pathol. 144.4(1994):820-828 9 pages.

Nilsson et al., "Evidence for Multiple Thyroxine-binding Sites in Human Prealbumin", J. Biol. Chem., 246(19):6098-6105 (1971) 8 pages.

Ning et al., "Anti-integrin monoclonal antibody CNTO 95 enhances the therapeutic efficacy of fractionated radiation therapy in vivo", Mol. Cancer Ther., 7(6):1569-1578 (2008) 10 pages.

Oak et al., "Antiangiogenic properties of natural polyphenols from red wine and green tea", J. Nutr. Biochem., 16:1-8 (2005) 8 pages.

Okada et al., "A Quantitative in vivo Method of Analyzing Human Tumor-induced Angiogenesis in Mice Using Agarose Microencapsulation and Hemoglobin Enzyme-linked Immunosorbent Assay", Jpn. J. Cancer Res., 86(12):1182-1188 (1995) 7 pages.

Pages et al., "Signaling Angiogenesis via p42/p44 MAP Kinase Cascade", Ann. N.Y. Acad., Sci., 902:187-200 (2000) 14 pages.

Painter et al., "Membrane initiation of DNA synthesis", Nature, 270:543 (1977) 1 page.

(56) References Cited

OTHER PUBLICATIONS

Panter et al., "Pretreatment with NMDA antagonists limits release of excitatory amino acids following traumatic brain injury", Neurosci. Lett., 136(2):165-168 (1992) 4 pages.
Panyam, et al., "Biodegradable nanoparticles for drug and gene delivery to cells and tissues", Advanced Drug Delivery Reviews, 55: 329-347 (2009) 19 pages.
Pardridge, W.M., "Receptor-Mediated Peptide Transport through the Blood-Brain Barrier", Endocrine Rev., 7(3):314-330 (1986) 18 pages.
Park et al., "Effects of Tetramethoxystilbene on Hormone-Resistant Breast Cancer Cells: Biological and Biochemical Mechanisms of Action", Cancer Res., 67:5717-5726 (2007) 10 pages.
Parveen, et al., "Polymeric nanoparticles for cancer therapy", Journal of Drug Targeting, 16(2): 108-123, Feb. 2008. 16 pages.
Patel, D.K., "Clinical Use of Anti-Epidermal Growth Factor Receptor Monoclonal Antibodies in Metastatic Colorectal Cancer", Pharacotherapy, 28(11 Pt.2):31S-41S (2008) 12 pages.
Penno et al., "Rapid and quantitative in vitro measurement of cellular chemotaxis and invasion", Meth. Cell Sci., 19:189-195 (1997) 7 pages.
Pirola, et al., "Resveratrol: One Molecule, Many Targets", IUBMB Life, vol. 60, Issue 5, pp. 323-332. 10 pages.
Plow et al., "Ligand Binding to Integrins", J. Biol. Chem., 275(29):21785-21788 (2000) 4 pages.
Powell, J., "The Serial Analysis of Gene Expression", in Meth. Mol. Biol., Chapter 20, 99:297-319 (2000) 23 pages.
Prichard et al., "Concurrent Cetuximab and Bevacizumab Therapy in a Murine Orthotopic Model of Anaplastic Thyroid Carcinoma", Laryngoscope, 117:674-679 (2007) 7 pages.
Pujol et al., "Letter to the editors: Preventioon of thyroid neoplasm recurrence with Triac and levothyroxine", Clin. Endocrinol., 46(1):121-122 (1997) 2 pages.
Raue et al., "Multiple Endocrine Neoplasia Type 2", Horm. Res., 68(Suppl.5): 101-104 (2007) 4 pages.
Rayalam et al., "Resveratrol induces apoptosis and inhibits adipogenesis in 3T3-L1 adipocytes", Phytother. Res., 22:1367-1371 (2008) 5 pages.
Rebbaa et al., "Novel function of the thyroid hormone analog tetraiodothyroacetic acide: a cancer chemosensitizing and anti-cancer agent", Angiogenesis, 11(3):269-276 (2008) 8 pages.
Reinholt et al., "Osteopontin—a possible anchor of osteoclasts to bone", Proc. Natl. Acad. Sci. U.S.A., 87:4473-4475 (1990) 3 pages.
Remsen et al., "Antibodies to the Neural Cell Adhesion Molecule Disrupt Functional Recovery in Injured Nerves", Exp. Neurol., 110:268-273 (1990) 6 pages.
Ren et al., "Regulation of tumor angiogenesis by thrombospondin-1", Biochim. Biophys. Acta. 1765: 178-188 (2006) 11 pages.
Risau, W., "Mechanisims of angiogenesis", Nature, 386:671-674 (1997) 4 pages.
Sahni et al., "Stimulation of endothelial cell proliferation by FGF-2 in the presence of fibrinogen requires $\alpha\beta3$", Blood, 104(12):3635-3641 (2004) 7 pages.
Saito et al., "Vector-mediated delivery of 125I-labeled β-amyloid peptide Aβ1-40 through the blood-brain barrier and binding to Alzheimer disease of the Aβ1-40/vector complex", Proc. Natl. Acad. Sci. US, 92:10227-10231 (1995) 5 pages.
Samuels et al., "Depletion of L-3-5-3'-Triiodothyronine and L-Thyroxine in Euthyroid Calf Serum for Use in Cell Culture Studies of the Action of Thyroid Hormone", Endo., 105(1):80-85 (1979) 6 pages.
SAS/STAT Guide for Personal Computers, Version 6 Edition, p. 717 (1987) 3 pages.
Sato et al., "Neovascularization: General Remarks", Biotherapy, 15(6):631-636 (2001) (English Abstract) 6 pages.
Scanlan et al., "3-Iodothyronamine is an endogenous and rapid-acting derivative of thyroid hormone", Nat. Med., 10(6):638-642 (2004) 5 pages.
Scanlan et al., "Selective thyrmimetics: Tissue-selective thyroid hormone analogs", Curr. Opin. Drug Discov. Dev., 4(5):614-622 (2001) 9 pages.

Schlange et al., "Autocrine WNT signaling contributes to breast cancer cell proliferation via the canonical WNT pathway and EGFR transactivation", Breast Cancer Res., 9:R63 (2007) 15 pages.
Schlumberger et al., "New therapeutic approaches to treat medullary thyroid carcinoma", Nat. Clin. Prac. Endocrinol. Metab., 4(10):22-32 (2008) 11 pages.
Schnell et al., "Expression of alpha v beta 3 integrin in patients with high and low grade glioma", Proc. Amer. Assoc. Cancer Res., 47:226 (2006) Abstract Only. 5 pages.
Schnell et al., "Expression of Integrin $\alpha\beta3$ in Gliomas Correlates with Tumor Grade and Is not Restricted to Tumor Vasculature", Brain Pathol., 18:378-386 (2008) 9 pages.
Schreiber et al., "Hormone delivery systems to the brain-transhyretin", Exp. Clin. Endocrinol Diabetes, 103(2): 75-80 (1995) 7 pages.
Schueneman et al., "SU11248 Maintenance Therapy Prevents Tumor Regrowth after Fractionated Irradiation of Murine Tumor Models", Cancer Res., 63:4009-4016 (2003) 8 pages.
Shih et al., "Thyroid Hormone Promotes Serine Phosphorylation of p53 by Mitogen-Activated Protein Kinase", Biochem., 40:2870-2878 (2001) 10 pages.
Shih et al., "Disparate Effects of Thyroid Hormone on Actions of Epidermal Growth Factor and Transforming Growth Factor-α Are Mediated by 3,5'-Cyclic Adenosine 5'-Monophosphate-Dependent Protein Kinase II", Endo., 145(4):1708-1717 (2004) 10 pages.
Shih et al., "Inhibitory effect of epidermal growth factor on resveratrol-induced apoptosis in prostate cancer cells is mediated by protein kinase C-α", Mol. Cancer Ther., 3:1355-1363 (2004) 9 pages.
Shinohara et al., "Enhanced radiation damage of tumor vasculature by mTOR inhibitors", Oncogene, 24:5414-5422 (2005) 9 pages.
Skrovronsky et al., "In vivo detection of amyloid plaques in a mouse model of Alzheimer's disease", Proc. Natl. Acad. Sci US, 97(13):7609-7614 (2000) 6 pages.
Skuli et al., "$\alpha\beta3/\alpha\beta5$ integrins-FAK-RhoB: A Novel Pathway for Hypoxia Regulation in Glioblastoma", Cancer Res., 69*8):3308-3316 (2009) 9 pages.
Song et al., "Formulation and characterization of biodegradable nanoparticles for intravascular local drug delivery", J. Controlled Rel., 43:197-212 (1997) 16 pages.
Stefani et al., "The Effect of Resveratrol on a Cell Model of Human Aging", Ann. NY Acad. Sci., 1114:407-418 (2007) 12 pages.
Strieth, et al., "Antiangiogenic combination tumor therapy blocking α-integrins and VEGF-receptor-2 increases therapeutic effects in vivo", Int. J. Cancer, 119:423-431 (2006) 9 pages.
Sumi et al., "Wound healing using regenerative medicine", Surg. Front., 10(2):162-165 (2003) 4 pages.
Office Action (Mail Date Sep. 4, 2014) for U.S. Appl. No. 12/947,389, filed Nov. 16, 2010.
A.D.A.M. Medical Encyclopedia, www.ncbi.nlm.nih.gov/pubmedhealth/PMH0001308/, downloaded Jul. 12, 2012. 6 pages.
Abdollahi et al., "Inhibition of $\alpha\beta3$ Integrin Survival Signaling Enhances Antiangiogenic and Antitumor Effects of Radiotherapy", Clin. Cancer Research., 11(17):6270-6279 (2005) 10 pages.
Albert et al., "Integrin $\alpha\beta3$ Antagonist Cilengitide Enhances Efficacy of Radiotherapy in Endothelial Cell and Non-Small-Cell Lung Cancer Models", Int. J. Radiat. Oncol. Biol. Phys., 65(5):1536-1543 (2006) 8 pages.
Alexis et al., "Nonocclusive Common Carotid Artery Thrombosis in the Rat Results in Reversible Sensorimotor and Cognitive Behavorial Deficits", Stroke, 26:2338-2346 (1995) 16 pages.
Ali et al., "Angiogenesis as a potential biomarker in prostate cancer chemoprevention trials", Urology, 57(Suppl 4A):143-147 (2001) 5 pages.
Ali et al., "Apoptosis-Inducing effect of erlotinib is potentiated by 3,3'-diindolylmethane in vitro and in vivo using an orthotopic model of pancreatic cancer", Mol. Cancer Ther., 7(6):1708-1719(2008) 12 pages.
Ali et al., "High levels of oestrogen receptor-α in tumorigenesis: inhibition of cell growth and angiogenic factors", Cell Prolif., 34(4):223-231 (2001) 10 pages.
Allen, A.R., "Surgery of experimental lesion of spinal cord equivalent to crush injury of fracture dislocation of spinal column", J. Am. Med. Assoc., 57(11):878-880 (1911) 4 pages.

(56) References Cited

OTHER PUBLICATIONS

Almog et al., "Transcriptional Switch of Dormant Tumors to Fast-Growing Angiogenic Phenotype", Cancer Res., 69(3):836-844 (2009).
Amirkhosravi et al., "Antimestatatic effect of tinzaparin, a low-molecular-weight heparin", J. Thromb. Haemost., 1:1972-1976 (2003) 5 pages.
Amirkhosravi et al., "Inhibition of tumor cell-induced platelet aggregation and lung metastasis by the oral GpIIb/IIIa antagonist XV454", J. Thrombosis and Haemostasis, 3:549-554 (2003) 6 pages.
Ando et al., "Induction by carbon-ion irradiation of the expression of vascular endothelial growth factor in lung carcinoma cells", Int. J. Radiat. Biol., 76(8):1121-1127 (2000) 7 pages.
Application No. PCT/US2004/030583, International Search Report and the Written Opinion of the International Searching Authority, or the Declaration dated Mar. 7, 2005. 11 pages.
Application No. PCT/US2005/032813, International Search Report dated Dec. 22, 2006. 6 pages.
Application No. PCT/US2007/009026, International Search Report dated Nov. 7, 2008. 5 pages.
Application No. PCT/US2009/069104, International Search Report dated Mar. 4, 2010 5 pages.
Application No. PCT/US2007/026167, International Search Report dated Oct. 30, 2008. 3 pages.
Application No. PCT/US2010/038700, International Search Report dated Mar. 21, 2011. 4 pages.
Application No. PCT/US2006/036243, International Search Report dated Jul. 30, 2007. 7 pages.
Application No. PCT/US2010/029371, International Search Report dated Aug. 24, 2010. 5 pages.
Audus et al., "Bovine Brain Microvessel Endothelial Cell Monolayers as a Model System for the Blood-Brain Barrier", in Biological Approaches to the Controlled Delivery of Drugs, Ann. N.Y. Acad. Sci., 507:9-18 (1987) 11 pages.
Avis, K.E., "Parenteral Preparations", in Remington's Pharmaceutical Sciences, 15th Ed., Chapter 84, pp. 1461-1487, Mack Publishing Co., Easton, Pennsylvania (1975) 29 pages.
Balestrazzi et al., "Leaf-associated bacteria from transgenic white poplar producing resveratrol-like compounds: isolation, molecular characterization, and evaluation of oxidative stress tolerance", Can. J. Microbiol., 55:829-840 (2009) 12 pages.
Balin-Gauthier et al., "In vivo and in vitro antitumor activity of oxaliplatin in combination with cetuximab in human colorectal tumor cell lines expressing different level of EGFR", Cancer Chemother. Pharmacol., 57:709-718 (2006) 8 pages.

Baur et al., "Resveratrol improves health and survival of mice on a high-calorie diet", Nature, 444:337-342 (2006) 6 pages.
Baur et al., "Therapeutic potential of resveratrol: the in vivo evidence", Nat. Rev. Drug Discov., 5:493-506 (2006) 14 pages.
Bederson et al., "Rat Middle Cerebral Artery Occlusion: Evaluation of the Model and Development of a Neurologic Examination", Stroke, 17(3):472-476 (1986) 6 pages.
Belenky et al., "NAD+ metabolism in health and disease", Trends Biochem. Sci., 32(1):12-19 (2007) 9 pages.
Benedetti et al., "Life Tables and Survivor Functions", in BMDP Statistical Software Manual, BMDP Statistical Software, Inc, vol. 2, p. 573 and 689-718 (1988) 33 pages.
Ben-Hur et al., "Thermally Enhanced Radioresponse of Cultured Chinese Hamster Cells: Inhibition of Repair of Sublethal Damage and Enhancement of Lethal Damage", Radiat Res., 58:38-51 (1974) 14 pages.
Bennett et al., "A peptide derived from α-fetoprotein prevents the growth of estrogen-dependent human breast cancers sensitive and resistant to tamoxifen", Proc. Natl, Acad. Sci. USA, 99(4):2211-2215 (2002) 5 pages.
Surks, Martin I. et al. "Subclinical Thyroid Disease; Scientific Review and Guidelines for Diagnosis and Management." Journal of the American Medical Association, Jan. 14, 2004, vol. 291, No. 2, pp. 228-238; especially p. 230-231.
Application No. PCT/US2010/038700, Supplemental European Search Report dated Apr. 20, 2015. 7 pages.
NCI Cancer Drug Information, Cetuximab, 2006,http://www.cancer.gov/cancertopics/druginfo/cetuximab,downloaded Jul. 18, 2014.
Gu et al. 2007, Nanotoday 2:14-21.
J Wood, K Bonjean, S Ruetz, A Bellahcene, L Devy, JM Foidart, V Castronovo, JR Green. "Novel Antiangiogenic Effects of the u Bisphosphonate Compound Zoledronic Acid." The Journal of Pharmacology and Experimental Therapeutics, vol. 302, No. 3, 2002, pp. 1 055-1 061.
M Yalcin, DJ Bharali, L Lansing, E Dyskin, SS Mousa, A Hercbergs, FB Davis, PJ Davis, SA Mousa. "Tetraidothyroacetic Acid v (Tetrac) and Tetrac Nanoparticles Inhibit Growth of Human Renal Cell Carcinoma Xenografts." Anticancer Research, vol. 29, 2009, pp. 3825-3832.
Notice of Allowance (Mail Date Aug. 3, 2015) for U.S. Appl. No. 14/078,713, filed Nov. 13, 2013.
Notice of Allowance (Mail Date Jul. 7, 2015) for U.S. Appl. No. 12/751,375, filed Mar. 31, 2010.
European Office Action for EP Application No. 07867073.4, mailed on Jul. 16, 2015.

\* cited by examiner

Target Natural Products for Hydrolyzable/Non-Hydrolyzable Polymer Conjugation
Flavone Natural Products
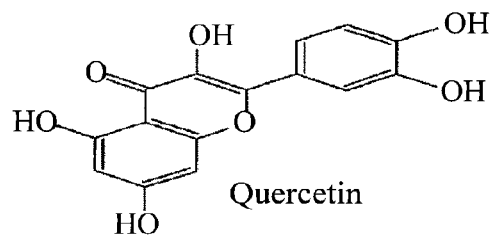
Quercetin
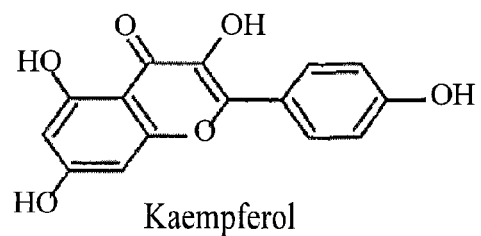
Kaempferol
Isoflavone Natural Products
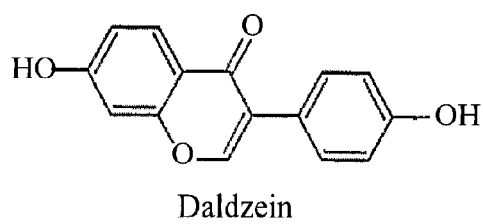
Daldzein
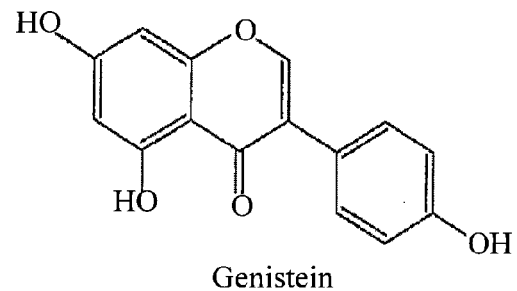
Genistein
Pterocarponoid Natural Products
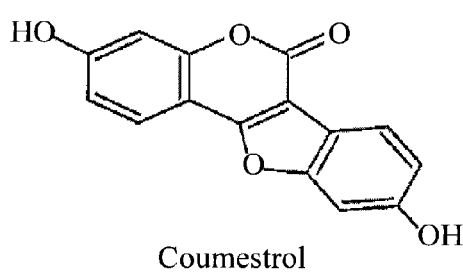
Coumestrol
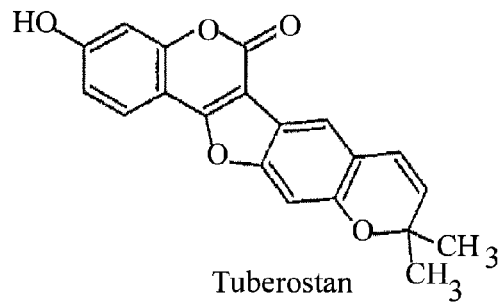
Tuberostan
FIG 1

Integrin αvβ3 Antagonists: Conjugation-Hydrolyzable/Retarded Release Conjugate-Synthesis & Targets
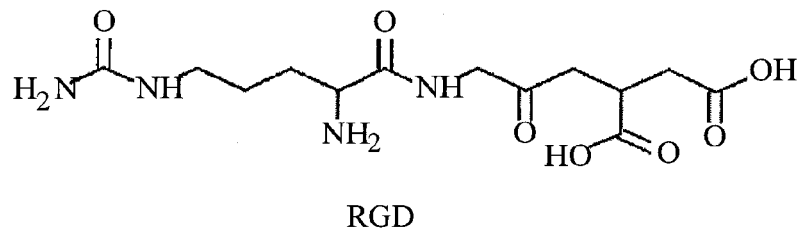
RGD
Some Selected Integrin Antagonists (Cylcic Peptide)
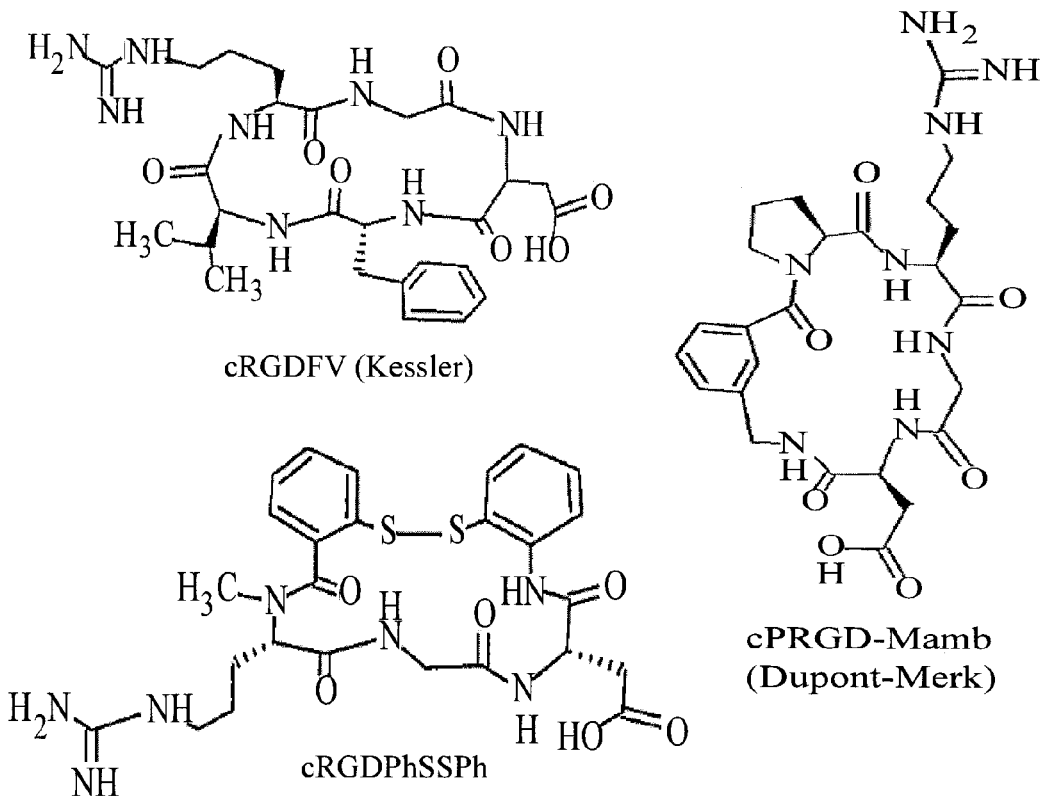
cRGDFV (Kessler)
cRGDPhSSPh
cPRGD-Mamb (Dupont-Merk)
FIG 2

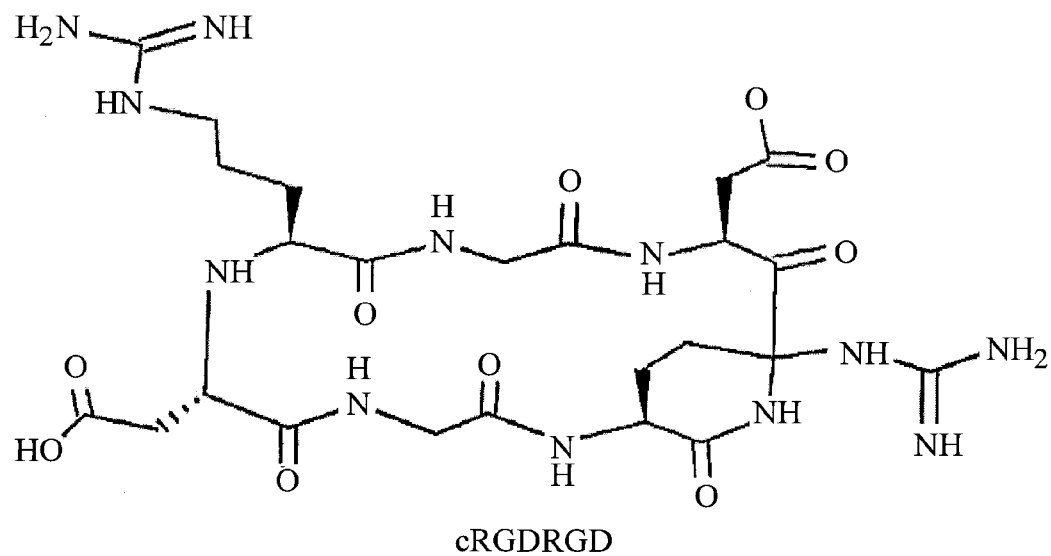
cRGDRGD
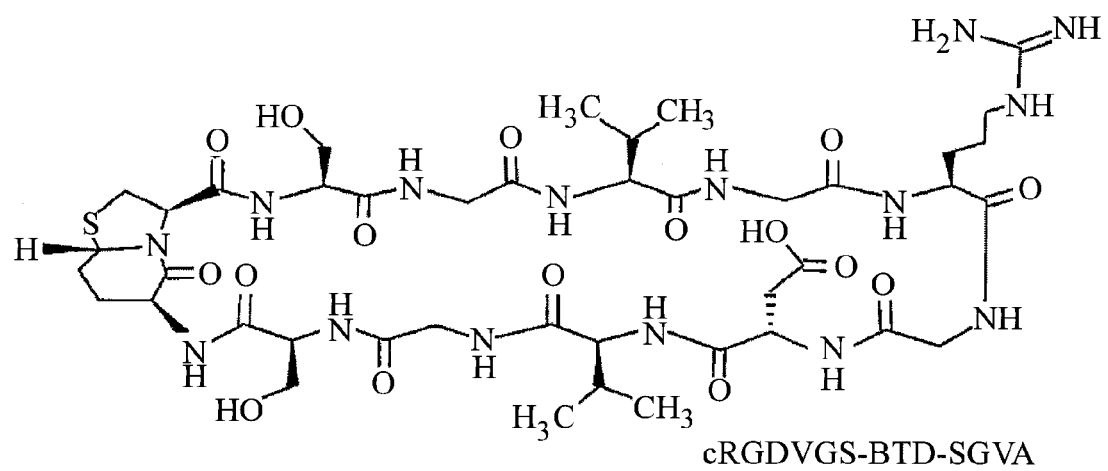
cRGDVGS-BTD-SGVA
FIG 3

Flavinoid Natural Products: Polymer Conjugation

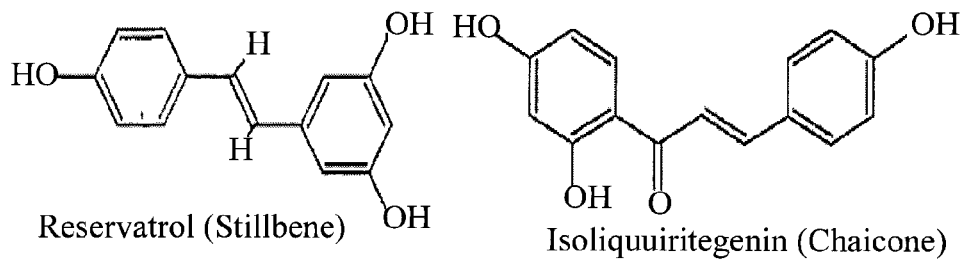

Reservatrol (Stillbene)         Isoliquuiritegenin (Chaicone)

Polymer Conjugates
PEG, m-PEG, Polyacrylic Acid Adducts

Mono and Multivariate Conjugates:
1. PEG-Resveratrol
2. PEG-Resveratrol-PEG
3. PEG-Resveratrol-PEG
   |
   PEG
4. Polyacrylic acid - Resveratrol Mono and Multivariate Conjugates:
1. PEG-Isoliquiritegenin
2. PEG-Isoliquiritegenin-PEG
3. PEG-Isoliquiritegenin-PEG
   |
   PEG

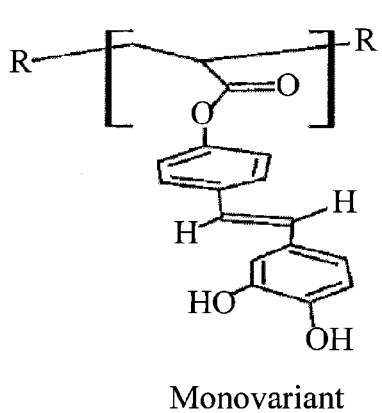
Monovariant

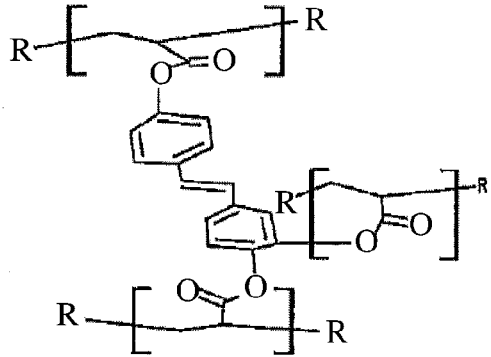
Multivariant

FIG 4

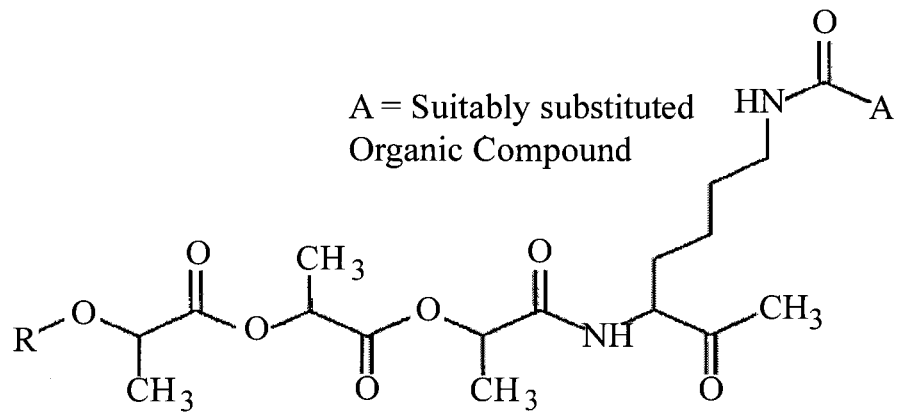
Poly-(lactide-co-lysine) immobilized conjugate
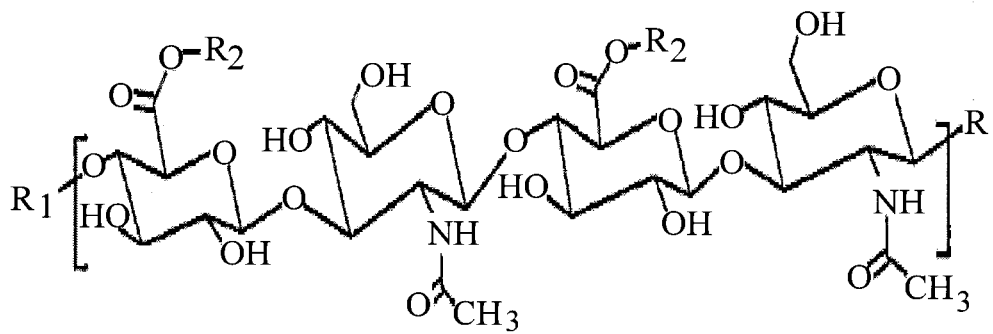
R1 = Hyaluronic acid chain
R2 = Flavinoids or NHS Ester linker mediated conjugation
Hyaluronic acid based hydrolysable & Non-slow Hydrolysable Flavinoid Conjugate
FIG. 6

Polymer or Protein bound Catechin or Epicatechin

METHODS OF STIMULATING FAT MOBILIZATION USING A POLYMER CONJUGATED POLYPHENOL

FIELD OF THE INVENTION

The invention described herein pertains to compounds and methods for the prevention or treatment of conditions associated with metabolic syndrome, and more particularly to the use of resveratrol-like compounds in the treatment of such conditions.

BACKGROUND

Metabolic syndrome (or Syndrome X) is characterized by a group of metabolic risk factors in one person that include, for example, central obesity (i.e., excessive fat tissue in and around the abdomen), atherogenic dyslipidemia (i.e., blood fat disorders—mainly high triglycerides and low HDL cholesterol—that foster plaque buildups in artery walls), raised blood pressure (e.g., 130/85 mmHg or higher), insulin resistance or glucose intolerance (the body can't properly use insulin or blood sugar), prothrombotic state (e.g., high fibrinogen or plasminogen activator inhibitor in the blood), and pro inflammatory state (e.g., elevated high-30 sensitivity C-reactive protein in the blood).

The underlying causes of this syndrome are overweight/obesity, physical inactivity and genetic factors. People with the metabolic syndrome are at increased risk of coronary heart disease, other diseases related to plaque buildups in artery walls (e.g., stroke and 35 peripheral vascular disease) and type 2 diabetes.

Metabolic syndrome has become increasingly common in the United States. It's estimated that about 47 million U.S. adults have it. The syndrome is closely associated with a generalized metabolic disorder called insulin resistance, in which the body cannot use insulin efficiently. This is why the metabolic syndrome is also called the insulin resistance syndrome. Some people are genetically predisposed to insulin resistance. Acquired factors, such as excess body fat and physical inactivity, can elicit insulin resistance and the metabolic syndrome in these people. Most people with insulin resistance have central obesity. The biologic mechanisms at the molecular level between insulin resistance and metabolic risk factors are not fully understood and appear to be complex.

Conventional treatment typically includes dietary changes to limit fat and calories, increased exercise, and changes in habits or patterns of eating. Medications commonly prescribed for weight loss include numerous metabolic stimulants, perhaps in combination with cholesterol lowering drugs and/or high blood pressure medications. However, such compounds may not be effective in all subjects, or may be of limited efficacy. Accordingly, new treatments for metabolic syndrome and its associated factors are needed.

Caloric restriction is known to extend lifespan in mammals. Caloric restriction also reduces the incidence of age-associated conditions such as obesity, insulin resistance, dyslipidemia, and cancer. Resveratrol, a polyphenol derived from red wine, is a "phytoestrogen" that mimics caloric restriction by activating Sir2 and extending lifespan in several species. Resveratrol is also known to have anti-inflammatory and anti-angiogenic effects, as well as preventive effects to atherosclerosis.

Resveratrol has been shown to reduce fat accumulation in C. elegans and in several insulin-sensitive mammalian cell lines Inhibition of AMP-activated kinase gene expression is also known to prevent the effect of reseveratrol on fat accumulation. Accordingly, the effect of resveratrol on fat accumulation depends on Sir2.1. Thus, resveratrol-like compounds will prove useful in the prevention and treatment of diseases and risk factors associated with metabolic syndrome.

Consequently, it would be desirable to provide resveratrol analogs, resveratrol-like compounds, and polymers thereof, as well as methods of using such compounds in preventing and treating diseases and risk factors associated with metabolic syndrome.

SUMMARY

In view of the foregoing, it is an object of the present invention to provide resveratrol-like compounds and methods for preventing and/or treating diseases and risk factors associated with metabolic syndrome.

It is a further object of the invention to screen for resveratrol-like compounds It is yet a further object of the present invention to provide methods of preventing and/or treating such disorders by targeting one or more RGD sites in selected intracellular or extracellular proteins.

Accordingly, these and other objects are accomplished by providing compounds and methods for preventing and/or treating diseases and risk factors associated with metabolic syndrome. In one aspect, the invention includes a compound that binds an RGD sequence is provided for the treatment of conditions associated with metabolic syndrome. The compound can include, but is not limited to, a polyphenol such as resveratrol, fisetin, butein, piceatannol, or quercetin, conjugated to a polymer.

In certain embodiments, the polymer can include, for example, polyvinyl alcohol, polyacrylic acid, polylactic acid, polyamidoamine and other polymers with different molecular weight ranging from 2,000-20,000 Dalton.

In another aspect, the invention includes a compound that binds an RGD sequence and inhibits insulin/integrin-signaling to fat cell differentiation and fat cell accumulation. The compound can include, but is not limited to, resveratrol conjugated to a polymer, encapsulated inside or immobilized on nanoparticles, or mimetics and analogs or polymers thereof.

In another aspect, the invention includes methods of treating conditions associated with metabolic syndrome by administering a therapeutically effective amount of a compound that inhibits insulin-integrin-signaling via one or more intracellular lipogenic proteins, or one or more extracellular proteins, containing the RGD sequence. In particular embodiments, the insulin/integrin-signaling intracellular protein can include, for example, sirtuins, phosphoinositide 3-kinase (PI3 kinas), or SREBP. In other embodiments, the insulin-integrin-signaling extracellular protein can include, for example, IGFBP-1, VEGF, or osteopontin.

The invention also provides methods for identifying target peptides possessing RGD-containing binding sites by providing an affinity column containing at least one resveratrol-like compound or anti-angiogenic compound, contacting the target peptide with the affinity column, and collecting the target peptides that bind to the resveratrol-like compound or anti-angiogenic compound.

In still another aspect, the invention provides methods for identifying genes that are regulated in opposing directions by insulin and an RGD-binding compound by selectively stimulating expression of an unknown gene product that encodes the RGD sequence, isolating the gene product from control cells, resveratrol-stimulated cells and insulin-stimulated cells, alone and in combination, and analyzing the pools of gene product to identify genes regulated in opposing directions by insulin and RGD-binding compounds. In particular embodiments, the gene products can include, for example, mRNA or protein. In further embodiments, the analyzing step can include performing a gene expression microarray or mass spectroscopy to identify RGD containing gene products.

The invention further provides methods of screening a test compound for modulating insulin sensitivity via an intracellular protein containing an RGD sequence, via an extracellular protein containing an RGD sequence, or by using the promoter of a gene product that encodes the RGD sequence. In screening a test compound for modulating insulin sensitivity via an intracellular protein containing an RGD sequence, the method includes providing a transformed cultured cell line overexpressing a recombinant expression construct containing at least one RGD protein, and another transformed cultured cell line overexpressing a mutant derivative bearing RGE, adding a test compound to each of the cell cultures, assaying the cell cultures to determine whether the test compound is imported into the cell lines, assaying the cell cultures to determine whether the desired phenotypic change has occurred in wild-type but not mutant cell lines, and binding the test compound to the wild-type protein, but not the mutant protein, in vitro, wherein binding of the test compound to the wild-type protein indicates that the protein modulates insulin activity.

In screening a test compound for modulating insulin sensitivity via an extracellular protein containing an RGD sequence, the method includes providing a cultured preadipocyte cell line, adding the protein containing an RGD sequence and a mutant protein containing an RGD sequence to the preadipocyte cell culture, assaying the transformed cells to determine whether the desired phenotypic change has occurred in wild-type but not mutant proteins, adding the test compound in the presence and absence of the RGD and RGE containing proteins, assaying the transformed cell line to determine whether the test compound prevents fat cell differentiation and/or fact accumulation, and determining whether the test compound binds to the wild-type but not the mutant protein, wherein binding of the test compound to the wild-type but not the mutant protein indicates that the test compound modulates insulin sensitivity by reducing adipogenesis.

In screening a test compound for modulating insulin sensitivity by using the promoter of a gene containing an RGD sequence, the method includes providing a cultured cell line with a reporter gene driven by the promoter of a gene product regulated at the transcription level by insulin or an RGD-binding compound, adding insulin to the cell culture, adding an RGD-binding compound to the cell culture, assaying the transformed cell to determine whether the effect of insulin on the promoter is inhibited by the RGD-binding compound, assaying libraries for a hit, and determining whether the test compound binds a wild-type but not a mutant protein, wherein binding indicates that the test compound modulates insulin sensitivity.

In still a further aspect, the invention provides methods for inhibiting the activity or expression of a protein containing an RGD sequence involved in the insulin-signaling pathway by administering an effective amount of an RGD-binding compound to a subject suffering from an insulin-signaling disorder and/or a disorder associated with metabolic syndrome. In certain embodiments, the insulin-signaling disorder includes, but is not limited to, obesity, insulin resistance, diabetes, and complication thereof such as hyperlipidemia, cardiovascular disease, neurological disease, and renal disease. In other embodiments, the protein containing the RGD sequence is currently expressed, and the RGD-binding compound inhibits the active protein as well as the syntheses of new proteins containing the RGD sequence. In further embodiments the RGD-binding compound inhibits the activities and/or processes that regulate fat cell differentiation and fat accumulation.

Other features and advantages of the invention will be apparent from the detailed description and the claims.

BRIEF DESCRIPTION OF THE DRAWINGS

FIG. 1 Representative polyphenols.
FIG. 2 Representative RGD analogs.
FIG. 3 Additional examples of RGD analogs.
FIG. 4 Polymer conjugates of polyphenolic compounds.
FIG. 6 Additional examples of polymer conjugates.

DETAILED DESCRIPTION

Figure 5:
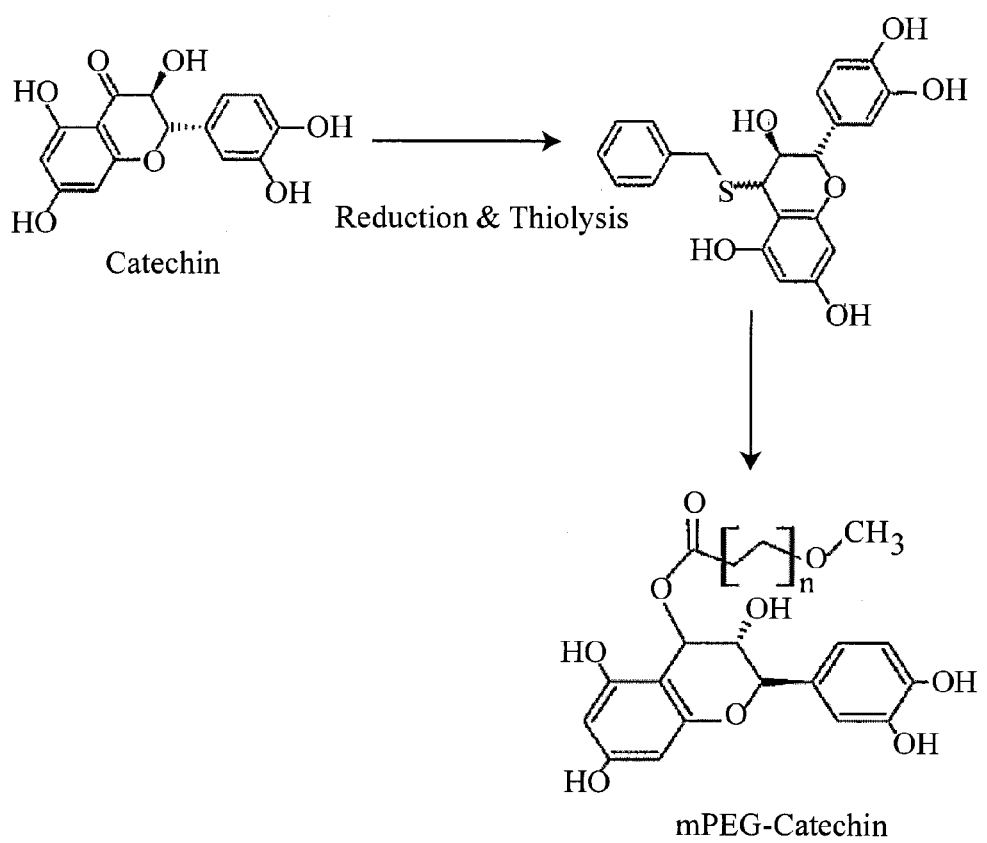
FIG. 5 Synthesis of polyphenolic polymer conjugates.

The details of one or more embodiments of the invention have been set forth in the accompanying description below. Although any methods and materials similar or equivalent to those described herein can be used in the practice or testing of the present invention, the preferred methods and materials are now described. Other features, objects, and advantages of the invention will be apparent from the description and from the claims. In the specification and the appended claims, the singular forms include plural references unless the context clearly dictates otherwise. All patents and publications cited in this specification are incorporated by reference in their entirety.

For convenience, certain terms used in the specification, examples and claims are collected here. Unless otherwise defined, all technical and scientific terms used herein have the same meaning as commonly understood by one of ordinary skill in the art to which this 30 invention pertains.

The term "agent" is used herein to denote a chemical compound, a mixture of chemical compounds, a biological macromolecule (such as a nucleic acid, an antibody, a protein or portion thereof, e.g., a peptide), or an extract made from biological materials such 35 as bacteria, plants, fungi, or animal (particularly mammalian) cells or tissues. The activity of such agents may render it suitable as a "therapeutic agent" which is a biologically, physiologically, or pharmacologically active substance (or substances) that acts locally or systemically in a subject.

The term "RGD" as used herein refers to the single letter amino acid code and references the tripeptide amino acid sequence arginine-glycine-aspartic acid (Arg-Gly-Asp).

The term "RGD-binding compound" is used herein to mean a compound that modulates at least one activity of a protein encoding the amino acid sequence Arg-Gly-Asp.

The terms "peptide mimetic", "mimetic", or "peptidomimetic" as used herein refer to a compound that mimics at least one activity of a peptide or compound. For example, an RGD-binding compound mimetic refers to a compound that mimics a compound that modulates at least one activity of a protein encoding the amino acid sequence Arg-Gly-Asp.

A "form that is naturally occurring" when referring to a compound means a compound that is in a form, e.g., a composition, in which it can be found naturally. For example, since resveratrol can be found in red wine, it is present in red wine in a form that is naturally occurring. A compound is not in a form that is naturally occurring if, e.g., the compound has been purified and separated from at least some of the other molecules that are found with the compound in nature. A "naturally occurring compound" refers to a compound that can be found in nature, i.e., a compound that has not been designed by man. A naturally occurring compound may have been made by man or by nature.

"Sirtuin protein" refers to a member of the sirtuin deacetylase protein family or preferably to the Sir2 family, which include yeast Sir2 (GenBank Accession No. P53685), *C. elegans* Sir-2.1 (GenBank Accession No. NP_501912), and human SIRTI (GenBank Accession No. NM_012238 and NP_036370 (or AF083106), and SIRT2 (GenBank Accession No. NM_030593 and AF083 107) proteins. Other family members include the four additional yeast Sir2-like genes termed "HST genes" (homologues of Sir two) HST1, HST2, HST3 and HST4, and the five other human homologues hSIRT3, hSIRT4, hSIRT5, hSIRT6 and hSIRT7 (Brachmann et al. (1995) Genes Dev. 9:2888 and Frye et al. (1999) BBRC 260:273). Preferred sirtuins are those that share more similarities with SIRT1, i.e., hSIRT1, and/or Sir2 than with SIRT2, such as those members having at least part of the N-terminal sequence present in SIRTI and absent in SIRT2 such as SIRT3 has.

"Diabetes" refers to high blood sugar or ketoacidosis, as well as chronic, general metabolic abnormalities arising from a prolonged high blood sugar status or a decrease in glucose tolerance. "Diabetes" encompasses both the type I and type II (Non Insulin Dependent Diabetes Mellitus or NIDDM) forms of the disease. The risk factors for diabetes include the following factors: waistline of more than 40 inches for men or 35 inches for women, blood pressure of 130/85 mmHg or higher, triglycerides above 150 mg/dl, fasting blood glucose greater than 100 mg/dl or high-density lipoprotein of less than 40 mg/dl in men or 50 mg/dl in women.

The term "hyperinsulinemia" refers to a state in an individual in which the level of insulin in the blood is higher than normal.

The term "insulin resistance" refers to a state in which a normal amount of insulin 15 produces a subnormal biologic response relative to the biological response in a subject that does not have insulin resistance.

The term "metabolic syndrome" or "disorders or conditions associated with metabolic syndrome," as discussed herein, refers to any disease or condition that is caused by or contributed to by insulin resistance. Examples include: diabetes, obesity, insulin-resistance syndromes, syndrome X, insulin resistance, high blood pressure, hypertension, high blood cholesterol, dyslipidemia, hyperlipidemia, dyslipidemia, atherosclerotic disease including stroke, coronary artery disease or myocardial infarction, hyperglycemia, hyperinsulinemia and/or hyperproinsulinemia, impaired glucose tolerance, delayed insulin release, diabetic complications, including coronary heart disease, angina pectoris, congestive heart failure, stroke, cognitive functions in dementia, retinopathy, peripheral neuropathy, nephropathy, glomerulonephritis, glomerulosclerosis, nephrotic syndrome, hypertensive enephrosclerosis, some types of cancer (such as endometrial, breast, prostate, and colon), complications of pregnancy, poor female reproductive health (such as menstrual irregularities, infertility, irregular ovulation, polycystic ovarian syndrome (peaS)), lipodystrophy, cholesterol related disorders, such as gallstones, cholescystitis and cholelithiasis, gout, obstructive sleep apnea and respiratory problems, osteoarthritis, and prevention and treatment of bone loss, e.g. osteoporosis.

"Obese" individuals or individuals suffering from obesity are generally individuals having a body mass index (BMI) of at least 25 or greater. Obesity mayor may not be associated with insulin resistance.

A "patient," "individual," "subject" or "host" refers to either a human or a non-human animal.

The term "modulation" is art-recognized and refers to up regulation (i.e., activation or stimulation), down regulation (i.e., inhibition or suppression) of a response, or the two in combination or apart.

The term "prophylactic" or "therapeutic" treatment is art-recognized and refers to administration of a drug to a host. If it is administered prior to clinical manifestation of the unwanted condition (e.g., disease or other unwanted state of the host animal) then the treatment is prophylactic, i.e., it protects the host against developing the unwanted condition, whereas if administered after manifestation of the unwanted condition, the treatment is therapeutic (i.e., it is intended to diminish, ameliorate or maintain the existing unwanted condition or side effects therefrom).

The term "mammal" is known in the art, and exemplary mammals include humans, primates, bovines, porcines, canines, felines, and rodents (e.g., mice and rats).

The term "pharmaceutically-acceptable salt" is art-recognized and refers to the relatively non-toxic, inorganic and organic acid addition salts of compounds, including, for example, those contained in compositions described herein.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof from one organ, or portion of the body, to another organ, or portion of the body. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as cornstarch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl Iaurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The terms "systemic administration," "administered systemically," "peripheral administration" and "administered peripherally" are art-recognized and refer to the administration of a subject composition, therapeutic or other material other than directly into 15 the central nervous system, such that it enters the patient's system and, thus, is subject to metabolism and other like processes.

The terms "parenteral administration" and "administered parenterally" are art-recognized and refer to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articulare, subcapsular, subarachnoid, intraspinal, and intrasternal injection and infusion.

"Treating" a condition or disease refers to curing as well as ameliorating at least one symptom of the condition or disease.

The term "therapeutic agent" is art-recognized and refers to any chemical moiety that is a biologically, physiologically, or pharmacologically active substance that acts locally or systemically in a subject. The term also means any substance intended for use in the diagnosis, cure, mitigation, treatment or prevention of disease or in the enhancement of desirable physical or mental development and/or conditions in an animal or human.

The term "therapeutic agent" is art-recognized and refers to a local or systemic effect in animals, particularly mammals, and more particularly humans caused by a pharmacologically active substance. The phrase "therapeutically-effective amount" means that amount of such a substance that produces some desired local or systemic effect at a reasonable benefit/risk ratio applicable to any treatment. The therapeutically effective amount of such substance will vary depending upon the subject and disease or condition being treated, the weight and age of the subject, the severity of the disease or condition, the manner of administration and the like, which can readily be determined by one of ordinary skill in the art. For example, certain compositions described herein may be administered in a sufficient amount to produce a desired effect at a reasonable benefit/risk ratio applicable to such treatment.

The term "synthetic" is art-recognized and refers to production by in vitro chemical or enzymatic synthesis.

Compositions

RGD is the single letter amino acid code for arginine-glycine-aspartate. This tripeptide motif can be found in proteins of the extracellular matrix. Integrins link the intracellular cytoskeleton of cells with the extracellular matrix by recognizing this RGD motif. Without attachment to the extracellular matrix, cells normally undergo apoptosis. Soluble RGD peptides induce apoptosis and might be used as drugs against angiogenesis, inflammation and cancer mestastasis since small soluble peptides containing the RGD motif inhibit cell attachment and consequently induce apoptosis.

Provided herein are RGD-binding compounds for treating a variety of conditions associated, directly or indirectly, with metabolic syndrome. Exemplary compounds include, but are not limited to, various polyphenols conjugated to a polymer. Polyphenols can include, for example, resveratrol, fisetin, butein, piceatannol, quercetin, and analogs thereof. In a preferred embodiment, the polyphenol is resveratrol or a resveratrol-like compound (i.e., a resveratrol analog).

Exemplary polymers that the polyphenols can be conjugated with include, but are not limited to polyvinyl alcohol, polyacrylic acid, polyethylene glycol, polylactic acid, hyaluronic acid, polyamidoamine and combinations thereof, with different molecular weight ranging from 2,000-20,000 Dalton. Acceptable polymers may also include poly(lactide-co-lysine) and methyl ether polyethylene glycol (m-PEG).

The RGD-binding compounds disclosed herein can also be used for preventing fat cell differentiation and/or fat accumulation. In addition to polymer conjugated resveratrol, or analogs thereof, RGD-binding compounds can include, for example, RGD, and analogs or polymers thereof. In one embodiment, a polymer conjugated RGD analog can include an integrin antagonist that inhibits angiogenesis.

Figure 7:
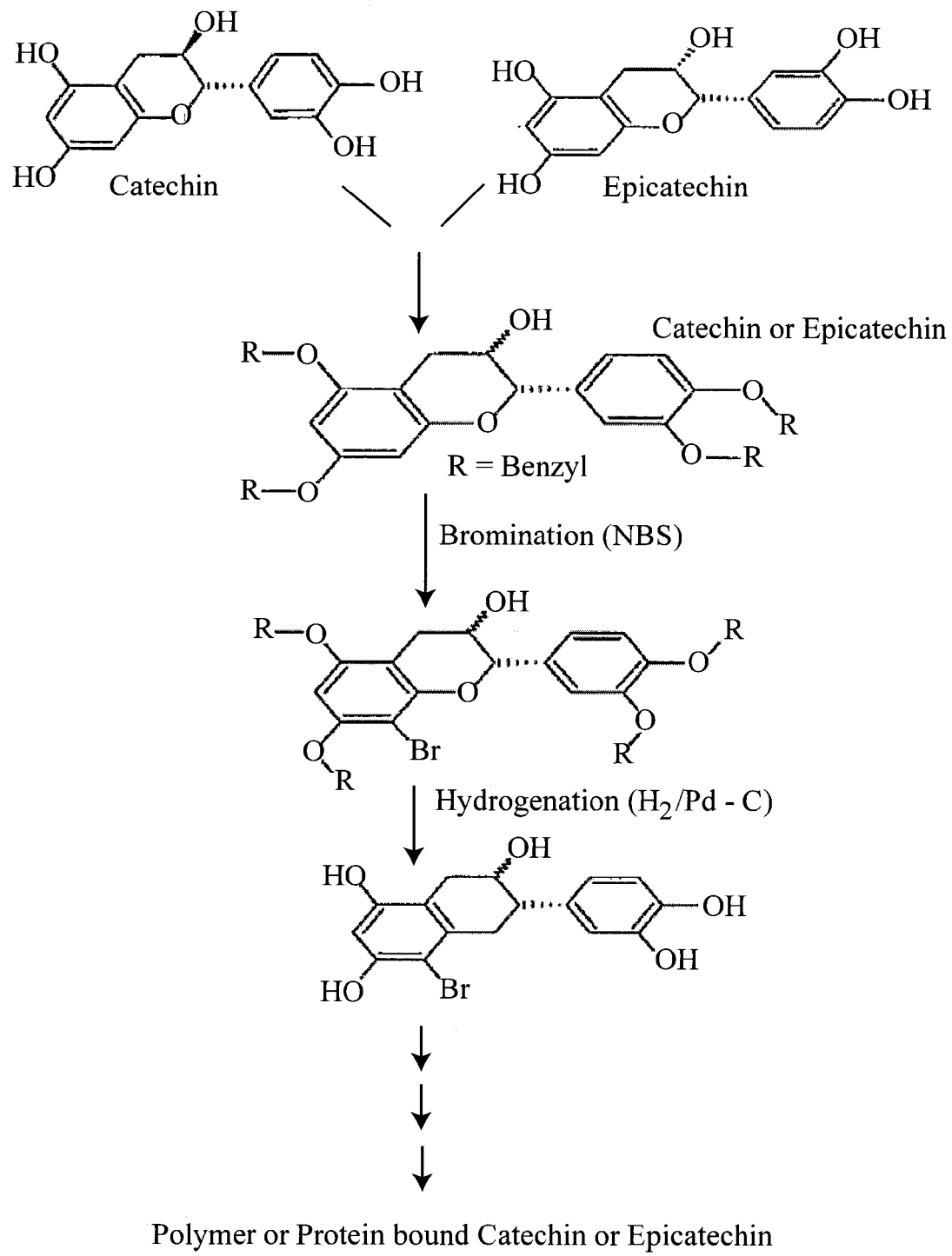
FIG. 7 Polymer or protein bound catechin/epicatechin.

Structure models for RGD-binding compounds contemplated by the present invention are more fully described in FIGS. 1-7.

The Role of Resveratrol or Resveratrol-like Compounds, Analogs, and Polymeric Conjugations in Affecting Insulin-Sensitivity Also provided herein are methods for treating a variety of conditions, directly or indirectly, associated with metabolic syndrome. In one embodiment, the method includes administering to a subject in need thereof a therapeutically effective amount of a compound that binds to one or more intra-cellular or extra-cellular lipogenic proteins encoding the amino acid sequence Arg-Gly-Asp (i.e., an RGD-binding compound). Such RGD-binding compounds inhibit insulin/integrin signaling, thereby treating conditions associated with metabolic syndrome.

Intra-cellular proteins contemplated by the present invention include, but are not limited to sirtuins, PI3 kinase, and sterol regulated binding protein-I ("SREBP-1"). Extracellular proteins contemplated by the present invention include, but are not limited to, insulin-like binding protein-1 ("igfbp-1"), vascular endothelial growth factor ("vegf"), and osteopontin As before, the compounds that bind the RGD sequence encoded by the intra-cellular or extra-cellular proteins include, for example, polymer conjugated resveratrol or analogs thereof, and RGD analogs and polymers thereof.

Screens for Identifying Peptides Encoding the Amino Acid Sequence Arg-Gly-Asp which Mediate the Adverse Effects of Conditions Associated with Metabolic Syndrome Also provided are methods for identifying target peptides encoding the amino acid sequence Arg-Gly-Asp. Such peptides often mediate the adverse effects of conditions associated with metabolic syndrome via signaling pathways, e.g., the insulin-signaling pathway or the integrin-signaling pathway. In one embodiment, the method can include providing an affinity column containing at least one compound that binds to the amino acid sequence Arg-Gly-Asp, contacting the target peptides with the at least one compound in the affinity column, and collecting the target peptides that bind to the compounds in the affinity column. Target peptides that bind to the compounds in the affinity column contain a functional RGD binding site.

In another aspect, methods for identifying genes encoding the amino acid sequence Arg-Gly-Asp that are regulated in opposing directions by insulin and at least one RGD-binding compound are provided. One method features selectively stimulating expression of an unknown gene product that encodes the amino acid sequence Arg-Gly-Asp, isolating the gene product from control, resveratrol- and insulin-stimulated cells alone and in combination, pooling the gene products, and analyzing the pools of gene product to identify genes regulated in opposing directions by insulin and at least one ROD-binding compound. In a preferred embodiment of the method, the analyzing step includes performing a gene expression microarray. In another embodiment, the analyzing step includes performing mass spectroscopy. The gene product can be mRNA or a protein.

Also provided are methods of screening for indicators of insulin sensitivity that encode the amino acid sequence Arg-Gly-Asp. One method includes providing an affinity column containing at least one compound that binds to the amino acid sequence Arg-Gly-Asp, introducing serum collected from a subject exposed to nutritional manipulations, or from a subject afflicted with a condition associated with metabolic syndrome to the column, wherein the serum contains at least one indicator of insulin sensitivity, and collecting at least one indicator that binds to the compounds in the affinity column. An indicator that binds to the compounds in the affinity column encodes the amino acid sequence Arg-Gly-Asp and represents an indicator of insulin sensitivity. In a preferred embodiment, the indicators are extra-cellular secretory proteins.

Screens for Identifying Resveratrol-like Compounds which Bind to Peptides Encoding the Amino Acid Sequence Arg-Gly-Asp In a further aspect, the invention also provides methods of screening a test compound for modulating insulin sensitivity. The target compound can modulate insulin activity by preventing insulin stimulated fat cell differentiation or insulin stimulated fat accumulation, or by potentiating insulin stimulated fat cell differentiation or insulin stimulated fat accumulation. One method includes providing a cell culture comprising a first cell line overexpressing a recombinant expression construct containing at least one intra-cellular protein encoding the amino acid sequence Arg-Gly-Asp, and a second cell line overexpressing a recombinant expression construct containing at least one mutant derivative of the protein expressed in said first cell line. The test compound can then be added to the cell culture and the cell culture assayed to determine whether the test compound is taken up by the first and second cell lines. The first and second cell lines can also be assayed to determine whether the test compound binds the protein expressed by the first and second cell line. Binding of the test compound to the protein expressed by the first cell line, but not the protein expressed by the second cell line, indicates that the test compound modulates insulin activity.

In a preferred embodiment of the method, the mutant derivative encodes the amino acid sequence Arg-Gly-Glu, which is different at only one amino acid location from the wild-type protein. In another embodiment, the first cell line in step (a) can alternatively contains an extra-cellular protein encoding the amino acid sequence Arg-Gly-Asp. The first and second cell line can contain, for example, preadipocytes.

In a further embodiment, the first cell line in step (a) can alternatively contain a reporter gene driven by the promoter of a gene product encoding the amino acid sequence Arg-Gly-Asp, whereas the second cell line in step (a) can alternatively contain a reporter gene driven by the promoter of a gene product encoding the amino acid sequence Arg-Gly-Glu (i.e., a mutant to the gene product expressed by the first cell line). This embodiment can further feature the step of adding insulin to the cell culture prior to adding the test compound to the cell culture. In a further embodiment, the assaying step can include determining whether the test compound binds the promoter expressed by the first and second cell line. Binding of the test compound to the promoter expressed by the first cell line, but not the promoter expressed by the second cell line, indicates that the test compound modulates insulin activity. Using this method, libraries of compounds can be screened to determine if the library contains compounds capable of binding to the amino acid sequence Arg-Gly-Asp, which is an indicator of a potential pharmaceutical that binds to proteins encoding the Arg-Gly-Asp amino acid sequence that mediates various signaling pathways in conditions associated with metabolic syndrome.

Methods for Inhibiting Peptides Encoding the Amino Acid Sequence Arg-Gly-Asp which Affect Insulin Sensitivity The present invention also provides methods for inhibiting the activity or expression of a protein encoding the amino acid sequence Arg-Gly-Asp. The method can include administering to a subject in need thereof an effective amount of an RGD-binding compound. In a preferred embodiment, the RGD-binding compound is polymer conjugated resveratrol, or analogs thereof.

A typical subject in need of administration of an RGD-binding compound as contemplated herein can include those suffering from a variety of conditions associated with metabolic syndrome. For example, the subject may be afflicted with anyone, or a combination, of the conditions selected from the group consisting of: insulin resistance, diabetes, obesity, insulin-resistance syndromes, syndrome X, high blood pressure, hypertension, high blood cholesterol, dyslipidemia, hyperlipidemia, atherosclerotic disease including stroke, coronary artery disease or myocardial infarction, hyperglycemia, hyperinsulinemia and/or hyperproinsulinemia, impaired glucose tolerance, delayed insulin release, diabetic complications, including coronary heart disease, angina pectoris, congestive heart failure, stroke, cognitive functions in dementia, retinopathy, peripheral neuropathy, nephropathy, glomerulonephritis, glomerulosclerosis, nephrotic syndrome, hypertensive enephrosclerosis, some types of cancer (such as endometrial, breast, prostate, and colon), complications of pregnancy, poor female reproductive health (such as menstrual irregularities, infertility, irregular ovulation, polycystic ovarian syndrome (PCOS)), lipodystrophy, cholesterol related disorders, such as gallstones, cholescystitis and cholelithiasis, gout, obstructive sleep apnea and respiratory problems, osteoarthritis, and prevention and treatment of bone loss, e.g. osteoporosis.

In one embodiment, the method is useful for inhibiting synthesis of new proteins encoding the amino acid sequence Arg-Gly-Asp, and/or inhibiting proteins that are currently expressed. Such proteins can be involved in the insulin-signaling and/or integrin-signaling pathways.

In another embodiment of the method, the RGD-binding compound regulates fat cell differentiation and/or fat accumulation by inhibiting a regulatory component involved in the activity or synthesis of the protein encoding the amino acid sequence Arg-Gly-Asp. The regulatory component can include, for example, anyone any one, or a combination, of a member selected from the group consisting of: insulin regulation, the effect of nutritional manipulation or inflammatory processes, hormone/nuclear receptor regulation, and coregulatory proteins that alter activity or synthesis of transcription factors that regulate fat cell differentiation and fat accumulation.

Formulations

The RGD-binding compounds described above are preferably administered in a formulation including analogs or polymeric forms, and derivatives together with an acceptable carrier for the mode of administration. Any formulation or drug delivery system containing the active ingredients, which is suitable for the intended use, as are generally known to those of skill in the art, can be used. Suitable pharmaceutically acceptable carriers for oral, rectal, topical or parenteral (including subcutaneous, intraperitoneal, intramuscular and intravenous) administration are known to those of skill in the art. The carrier must be pharmaceutically acceptable in the sense of being compatible with the other ingredients of the formulation and not deleterious to the recipient thereof.

Formulations suitable for parenteral administration conveniently include sterile aqueous preparation of the active compound, which is preferably isotonic with the blood of the recipient. Thus, such formulations may conveniently contain distilled water, 5% dextrose in distilled water or saline. Useful formulations also include concentrated solutions or solids containing the compound of formula (I), which upon dilution with an appropriate solvent give a solution suitable for parental administration above.

For enteral administration, a compound can be incorporated into an inert carrier in discrete units such as capsules, cachets, tablets or lozenges, each containing a predetermined amount of the active compound; as a powder or granules; or a suspension or solution in an aqueous liquid or non-aqueous liquid, e.g., a syrup, an elixir, an emulsion or a draught. Suitable carriers may be starches or sugars and include lubricants, flavorings, binders, and other materials of the same nature.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine, a mixture of the powdered active compound with any suitable carrier.

A syrup or suspension may be made by adding the active compound to a concentrated, aqueous solution of a sugar, e.g., sucrose, to which may also be added any accessory ingredients. Such accessory ingredients may include flavoring, an agent to retard crystallization of the sugar or an agent to increase the solubility of any other ingredient, e.g., as a polyhydric alcohol, for example, glycerol or sorbitol.

Formulations for rectal administration may be presented as a suppository with a 10 conventional carrier, e.g., cocoa butter or Witepsol S55 (trademark of Dynamite Nobel Chemical, Germany), for a suppository base.

Alternatively, the compound may be administered in liposomes or micro spheres (or microparticles). Methods for preparing liposomes and microspheres for administration to a patient are well known to those of skill in the art. U.S. Pat. No. 4,789,734, the contents of which are hereby incorporated by reference, describes methods for encapsulating biological materials in liposomes. Essentially, the material is dissolved in an aqueous solution, the appropriate phospholipids and lipids added, along with surfactants if required, and the material dialyzed or sonicated, as necessary. A review of known methods is provided by G. Gregoriadis, Chapter 14, "Liposomes," Drug Carriers in Biology and Medicine, pp. 287-341 (Academic Press, 1979).

Microspheres formed of polymers or proteins are well known to those skilled in the art, and can be tailored for passage through the gastrointestinal tract directly into the blood stream. Alternatively, the compound can be incorporated and the microspheres, or composite of micro spheres, implanted for slow release over a period of time ranging from days to months. See, for example, U.S. Pat. Nos. 4,906,474, 4,925,673 and 3,625,214, and Jein, TIPS19: 155-157 (1998), the contents of which are hereby incorporated by reference.

In one embodiment, the RGD-binding compounds or its polymeric forms can be formulated into nanoparticles.

Preferred nanoparticles are those prepared from biodegradable polymers, such as polyethylene glycols, polyglycolide, polylactide and copolymers thereof. Those of skill in the art can readily determine an appropriate carrier system depending on various factors, including the desired rate of drug release and the desired dosage.

In one embodiment, the formulations are administered via catheter directly to the inside of blood vessels. The administration can occur, for example, through holes in the catheter. In those embodiments wherein the active compounds have a relatively long half life (on the order of 1 day to a week or more), the formulations can be included in biodegradable polymeric hydrogels, such as those disclosed in U.S. Pat. No. 5,410,016 to Hubbell et al. These polymeric hydro gels can be delivered to the inside of a tissue lumen and the active compounds released over time as the polymer degrades. If desirable, the polymeric hydro gels can have microparticles or liposomes which include the active compound dispersed therein, providing another mechanism for the controlled release of the active compounds.

The formulations may conveniently be presented in unit dosage form and may be prepared by any of the methods well known in the art of pharmacy. All methods include the step of bringing the active compound into association with a carrier, which constitutes one or 15 more accessory ingredients. In general, the formulations are prepared by uniformly and intimately bringing the active compound into association with a liquid carrier or a finely divided solid carrier and then, if necessary, shaping the product into desired unit dosage form.

The formulations can optionally include additional components, such as various biologically active substances such as growth factors (including TGF-.beta., basic fibroblast growth factor (FGF2), epithelial growth factor (EGF), transforming growth factors .alpha. and .beta. (TGF alpha. and beta.), nerve growth factor (NGF), platelet-derived growth factor (PDGF), and vascular endothelial growth factor/vascular penneability factor (VEGF/VPF)), antiviral, antibacterial, anti-inflammatory, immuno-suppressant, analgesic, vascularizing agent, and cell adhesion molecule.

In addition to the aforementioned ingredients, the formulations may further include one or more optional accessory ingredient(s) utilized in the art of pharmaceutical formulations, e.g., diluents, buffers, flavoring agents, binders, surface active agents, thickeners, lubricants, suspending agents, preservatives (including antioxidants) and the like.

The invention will be further illustrated in the following non-limiting examples.

EXAMPLE 1

Size Measurement of Resveratrol Doped Poly(Lactic-co-glycolic Acid) (PLGA) or Poly(Lactic-co-glycolic Acid)/Polyvinyl Alcohol (PLGA/PVA) Nanoparticles by Dynamic Light Scattering (DLS)

Resveratrol nanoparticles were prepared. The size of the nanoparticles was determined by DLS (single emulsion/solvent evaporation method), and ranged from 100-300 nm. The surface of PLGA nanoparticles was coated with chitosan and/or PVA.

EXAMPLE 2

Polymer Conjugated Polyphenols Activate AMPK and Stimulate Fat Mobilization

Polyphenols, such as resveratrol, have beneficial effects on dyslipidemia, which accelerates atherosclerosis in diabetes. Using HEPG2 cell models or 3T3 adipocyte models it the polymer conjugated polyphenols described herein were observed to activate AMPK and stimulate fat mobilization. Specifically, the polymer conjugated polyphenols described herein increased phosphorylation of AMPK and its downstream target, acetyl-CoA carboxylase (ACC), and they increased activity of AMPK. The polymer conjugated polyphenols described herein also prevented the lipid accumulation that occurred in HepG2 cells exposed to high glucose. These studies demonstrate that the polymer conjugated polyphenols described and claimed herein are useful as a new therapeutic avenue to treat hyperlipidemia and atherosclerosis specifically in diabetes via activating AMPK.

Other Embodiments

While the invention has been described in conjunction with the detailed description 25 thereof, the foregoing description is intended to illustrate and not limit the scope of the inven-

What is claimed is:

1. A method of stimulating fat mobilization, the method comprising the steps of:
   providing a polyphenol;
   conjugating the polyphenol to a polymer selected from the group consisting of polyethylene glycol, polyglycolide, polylactide, polyvinyl alcohol, polyacrylic acid, hyaluronic acid and polyamidoamine;
   administering to a subject suffering from dyslipidemia, the polyphenol conjugated to the polymer; and
   binding the polyphenol conjugated to the polymer to a protein comprising an amino acid sequence Arg-Gly-Asp (RGD) recognition site, leading to increased phosphorylation of AMP kinase (AMPK), stimulating fat mobilization.

2. The method of claim 1, wherein the polyphenol is resveratrol.

3. The method of claim 1, wherein the polyphenol conjugated to the polymer inhibits the synthesis of new proteins comprising the amino acid sequence Arg-Gly-Asp.

4. The method of claim 1, wherein the polyphenol conjugated to the polymer regulates fat cell differentiation and/or fat accumulation by inhibiting a regulatory component involved in the activity or synthesis of the protein comprising the amino acid sequence Arg-Gly-Asp.

5. The method of claim 1, wherein the polymer is a nanoparticle between 100-300 nm.

* * * * *

UNITED STATES PATENT AND TRADEMARK OFFICE
CERTIFICATE OF CORRECTION

| | | |
|---|---|---|
| PATENT NO. | : 9,272,049 B2 | Page 1 of 1 |
| APPLICATION NO. | : 13/156047 | |
| DATED | : March 1, 2016 | |
| INVENTOR(S) | : Maria Alexander-Bridges et al. | |

It is certified that error appears in the above-identified patent and that said Letters Patent is hereby corrected as shown below:

In the Specification,

Column 2, line 1, please change "reseveratrol" to --resveratrol--

Column 10, line 34, please change "anyone" to --any one--

Signed and Sealed this
Fifth Day of July, 2016

Michelle K. Lee
*Director of the United States Patent and Trademark Office*